United States Patent
Kinoh et al.

(10) Patent No.: US 10,220,026 B2
(45) Date of Patent: Mar. 5, 2019

(54) MICELLE CONTAINING EPIRUBICIN-COMPLEXED BLOCK COPOLYMER AND ANTI-CANCER AGENT, AND PHARMACEUTICAL COMPOSITION CONTAINING SAID MICELLE APPLICABLE TO TREATMENT OF CANCER, RESISTANT CANCER OR METASTATIC CANCER

(71) Applicants: The University of Tokyo, Tokyo (JP); Tokyo Institute of Technology, Tokyo (JP)

(72) Inventors: Hiroaki Kinoh, Tokyo (JP); Kazunori Kataoka, Tokyo (JP); Horacio Cabral, Tokyo (JP); Yutaka Miura, Tokyo (JP); Shigeto Fukushima, Tokyo (JP); Nobuhiro Nishiyama, Tokyo (JP); Tsukasa Chida, Tokyo (JP)

(73) Assignees: THE UNIVERSITY OF TOKYO, Tokyo (JP); TOKYO INSTITUTE OF TECHNOLOGY, Tokyo (JP)

( * ) Notice: Subject to any disclaimer, the term of this patent is extended or adjusted under 35 U.S.C. 154(b) by 0 days.

(21) Appl. No.: 15/503,370

(22) PCT Filed: Aug. 11, 2015

(86) PCT No.: PCT/JP2015/072797
§ 371 (c)(1),
(2) Date: Feb. 10, 2017

(87) PCT Pub. No.: WO2016/024595
PCT Pub. Date: Feb. 18, 2016

(65) Prior Publication Data
US 2017/0258922 A1    Sep. 14, 2017

(30) Foreign Application Priority Data

Aug. 11, 2014 (JP) ................... 2014-163989

(51) Int. Cl.
| | | |
|---|---|---|
| A61K 31/4402 | (2006.01) | |
| A61K 31/4545 | (2006.01) | |
| A61K 31/475 | (2006.01) | |
| A61K 31/553 | (2006.01) | |
| A61K 31/704 | (2006.01) | |
| A61K 31/4375 | (2006.01) | |
| A61K 47/48 | (2006.01) | |
| A61K 9/00 | (2006.01) | |
| A61K 45/06 | (2006.01) | |
| A61K 47/60 | (2017.01) | |
| A61K 47/59 | (2017.01) | |
| A61K 47/69 | (2017.01) | |

(52) U.S. Cl.
CPC ........ *A61K 31/4402* (2013.01); *A61K 9/0019* (2013.01); *A61K 31/4375* (2013.01); *A61K 31/4545* (2013.01); *A61K 31/475* (2013.01); *A61K 31/553* (2013.01); *A61K 31/704* (2013.01); *A61K 45/06* (2013.01); *A61K 47/488* (2013.01); *A61K 47/59* (2017.08); *A61K 47/60* (2017.08); *A61K 47/6907* (2017.08)

(58) Field of Classification Search
CPC ............ A61K 31/4402; A61K 47/6907; A61K 47/60; A61K 47/59; A61K 9/0019; A61K 31/4375; A61K 31/475; A61K 31/553; A61K 31/704; A61K 45/06; A61K 47/488
See application file for complete search history.

(56) References Cited

U.S. PATENT DOCUMENTS

| | | | |
|---|---|---|---|
| 5,726,164 A | 3/1998 | Weder et al. | |
| 2008/0248097 A1* | 10/2008 | Kwon | A61K 9/1075 424/450 |
| 2010/0298495 A1 | 11/2010 | Bob et al. | |
| 2011/0201754 A1 | 8/2011 | Kitagawa et al. | |

FOREIGN PATENT DOCUMENTS

| | | |
|---|---|---|
| JP | H5-247055 A | 9/1993 |
| JP | H8-268893 A | 10/1996 |
| WO | 2008/047948 A1 | 4/2008 |
| WO | 2009/116509 A1 | 9/2009 |

OTHER PUBLICATIONS

PCT/JP2015/072797—International Search Report dated Sep. 15, 2015, 3 pages.
Bae, Y., et al., "Mixed Polymeric Micelles for Combination Cancer Chemotherapy Through the Concurrent Delivery of Multiple Chemotherapeutic Agents," Science Direct, Journal of Controlled Release 122, Jun. 13, 2007, pp. 327-300.
Beltran, P. J., et al., "Chemosensitization of Cancer Cells by the Saurosporine Derivative CGP 41251 in Association with Decreased P-Glycoprotein Phosphorylation," Biochemical Pharmacology, 1997, vol. 53, pp. 245-247 (Abstract, p. 245, left column, $5^{th}$ line from the bottom to right column, line 13, Figures 1 and 2, Table 1), Jan. 24, 1997 Elsevier Science Inc., 5 pages provided.
Castro, A. F., et al., "Mechanism of Inhibition of P-glycoprotein-Mediated Drug Transport by Protein Kinase C Blockers," Biochemical Pharmacology, vol. 58, pp. 1723-1733, May 21, 1999.
Koganzi, Chiryoyaku, Manual 2007, pp. 1429, 1477 to 1480, Feb. 1, 2007 (p. 1429, col. of 4. Shinkoki Igan, p. 1479, right column, $3^{rd}$ line from the bottom to p. 1480, left column, line 11), Partial English translation included, 8 pages provided.
Mukthavaram, R., et al., "High-Efficiency Liposomal Encapsulation of a Tyrosine Kinase Inhibitor Leads to Improved in Vivo Toxicity and Tumor Response Profile," International Journal of Nanomedicine, Dove Press, Oct. 18, 2013, vol. 8, pp. 3991-4006.

(Continued)

*Primary Examiner* — Alma Pipic
(74) *Attorney, Agent, or Firm* — Mintz, Levin, Cohn, Ferris, Glovsky and Popeo, P.C.

(57) ABSTRACT

The problem addressed by the present invention is to develop a pharmaceutical having therapeutic efficacy against epirubicin-resistant tumors. The present invention provides a micelle having an anti-cancer agent disposed inside the core of the micelle formed by an epirubicin-conjugated copolymer.

18 Claims, 18 Drawing Sheets

(56) References Cited

OTHER PUBLICATIONS

Si, M. S., et al., "Effects of the Kinase Inhibitor CGP41251 (PKC 412) on Lymphocyte Activation and TNF-alpha Production," International Immuno pharmacology, Feb. 14, 2005, vol. 5, Elsevier B.V., pp. 1141-1149.
Takahashi, A., et al, "NC-6300, An Epirubicin-Incorporating Micelle, Extends the Antitumor Effect and Reduces the Cardiotoxicity of Epirubicin," Cancer Science, the Official Journal of the Japanese Cancer Association, Jul. 2013, vol. 104, No. 7, first published Apr. 19, 2013, 6 pages provided.
Torti, F. M., et al., "Cardiotoxicity of Epirubicin and Doxorubicin: Assessment by Endomyocardial Biopsy," Cancer Research, Jul. 1986, vol. 46, pp. 3722-3727.
Utz, I., et al., "The Protein Klinase C Inhibitor CGP 41251, A Staurosporine Derivative with Antitumor Activity, Reverses Multidrug Resistance," Int. J. Cancer, 1994, vol. 57, pp. 104-110 (Abstract, p. 104, upper part, right column, lines 6 to 20), Apr. 1, 1994 Wiley-Liss Inc ., 9 pages provided.
Vingradov, S., et al., "Cancer Stem Cells and Drug Resistance: the Potential of Nanomedicine," Nanomedicine (Lond), Apr. 2012, vol. 7, No. 4, pp. 597-615 (Abstract, p. 3, lines 6 to 40), 20 pages provided.
Akinaga, Shiro et al., "Antitumor effect of KT6124, a novel derivative of protein kinase inhibitor K-252a, and its mechanism of action," *Cancer Chemother Pharmacol* (1992; Accepted Sep. 25, 1991); 29:266-272.
Boggon, Titus J. et al., "Crystal structure of the Jak3 kinase domain in complex with a staurosporine analog," *Blood* (Aug. 1, 2005) 106:996-1002.
Camoratto, Anna Marie et al., "CEP-751 Inhibits TRK Receptor Tyrosine Kinase Activity In Vitro and Exhibits Anti-Tumor Activity," *Int. J. Cancer* (Revised Apr. 3, 1997); 72:673-679.
Hachisu, Mitsugu et al., "Antihypertensive Compounds with Potent Protein Kinases Inhibitory Activity," *Life Sciences*, (Mar. 3, 1989); 44:1351-1362.

Huwiler, Andrea et al., "A role for protein kinase C-α in zymosan-stimulated eicosanoid synthesis in mouse peritoneal macrophages," *Eur. J. Biochem.* (Rec'd May 20/Jul. 5, 1993); 271:69-75.
Kohama, Kazuhiro et al., "Effects of NA0344, A New Smooth Muscle Relaxant, on the Actin-Myosin-ATP Interaction and Myosin Light Chain Phosphorylation In Vitro," *Gen. Pharmac.* (1991; Rec'd Jul. 26, 1990); 22(3):465-474.
Martiny-Baron, Georg et al., "Selective Inhibition of Protein Kinase C Isozymes by the Indolocarbazole GÖ 6976," *The Journal of Biological Chemistry* (May 5, 1993) 268(13):9194-9197.
Meggio, Flavio et al., "Different susceptibility of protein kinases to staurosporine inhibition Kinetic studies and molecular bases for the resistance of protein kinase CK2," *Eur. J. Biochem.* (Rec'd Aug. 25, 1995); 234:317-322.
Meyer, Thomas et al., "A Derivative of Staurosporine (CGP 41 251) Shows Selectivity for Protein Kinase C Inhibition and In Vitro Anti-Proliferative as Well as In Vivo Anti-Tumor Activity," *Int. J. Cancer* (1989; Rec'd in revise form Dec. 21, 1988); 43:851-856.
Nakanishi, Satoshi et al., "KT5926, a Potent and Selective Inhibitor of Myosin Light Chain Kinase," *Molecular Pharmacology* (Accepted Jan. 24, 1990); 37:482-488.
Reynolds, N. J. et al., "SCH 47112, a novel staurosporine derivative inhibits 12-0-tetradecanoylphorbol-13-acetate-induced inflammation and epidermal hyperplasia in hairless mouse skin," *Arch Dermatol Res* (1997; Rec'd Jul. 29, 1996); 289:540-546.
Sezaki, Masaji et al., "A New Antibiotic SF-2370 Produced by *Actinomadura,*" *The Journal of Antibiotics* (Rec'd Jun. 4, 1985); XXXVII(10):1437-1439.
Takahashi, Isami et al., "Potent Selective Inhibition of 7-O-Methyl UCN-01 against Protein Kinase C," *The Journal of Pharmacology and Experimental Therapeutics*, (Accepted for Pub Sep. 4, 1990); 255(3):1218-1221.
Tanida, Seiichi et al., "Tan-999 and Tan-1030A, New Indolocarbazole Alkaloids with Macrophage-Activating Properties," *The Journal of Antibiotics*, (Nov. 1989; Rec'd for Pub May 22, 1989); XLII(11):1619-1630.
Yamashita, Yoshinori et al., "Induction of Mammalian DNA Topoisomerase I Mediated DNA Cleavage by Antitutmor Indolocarbazole Derivatives," *Biochemistry* (Revised Manuscript Rec'd Sep. 8, 1992); 31(48):12069-12075.

\* cited by examiner

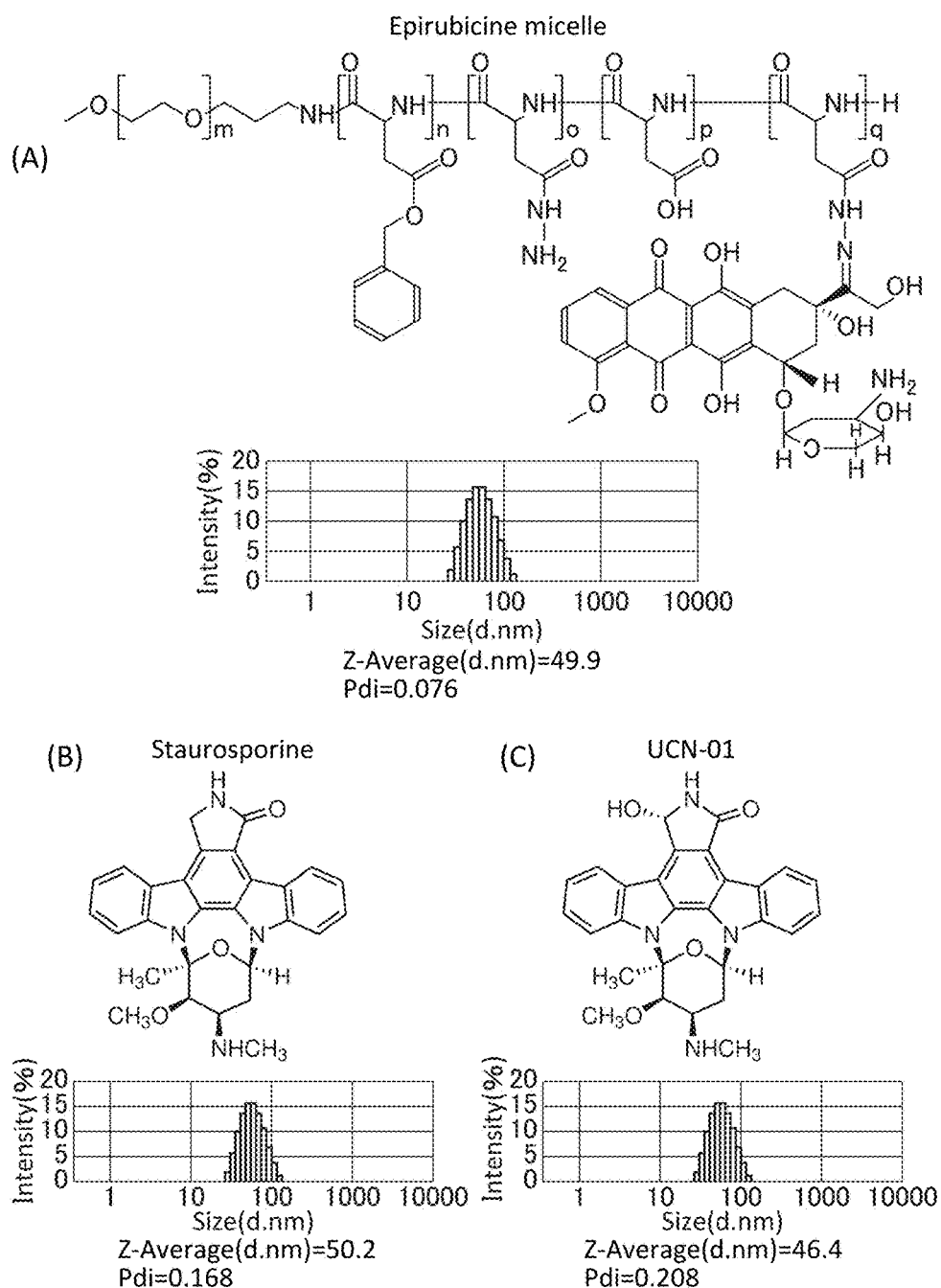
FIG. 1A-C

FIG. 1D-F
(D) Reserpine
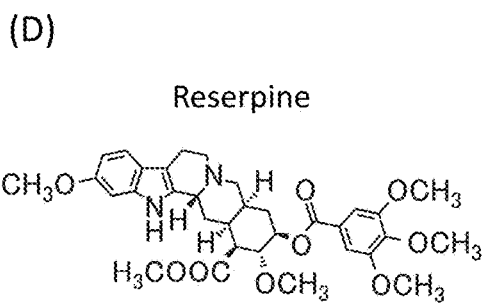
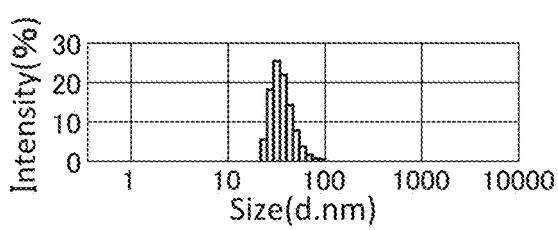
Z-AVERAGE(d.nm):60.19
PdI:0.138
(E) Lestarutinib (CEP-701)
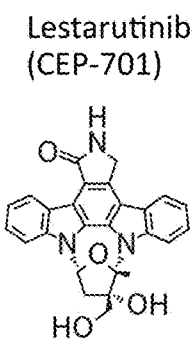
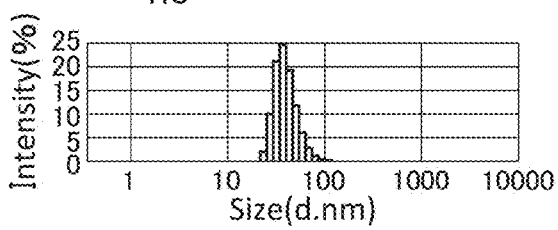
Z-AVERAGE(d.nm):65.95
PdI:0.112
(F) PKC412
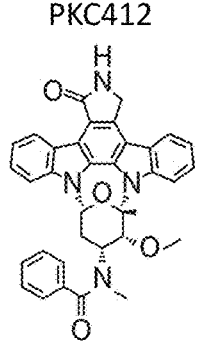
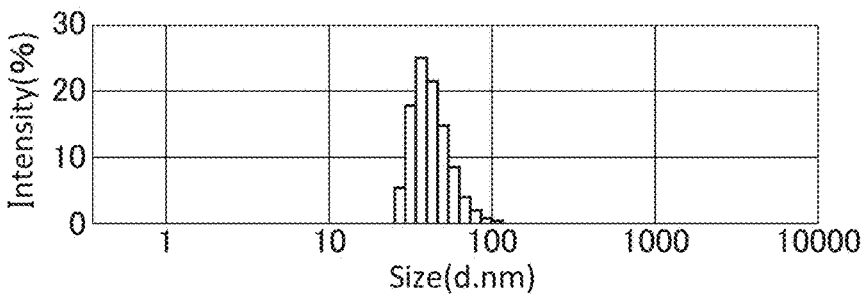
Z-AVERAGE(d.nm):70.2
PdI:0.163

FIG. 1G
(G)
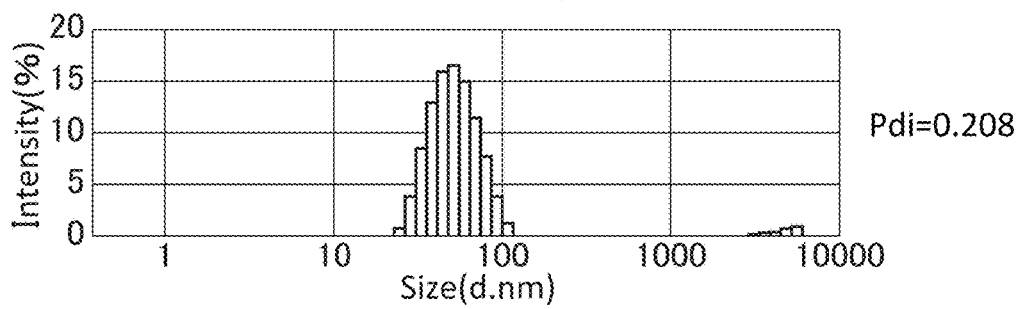
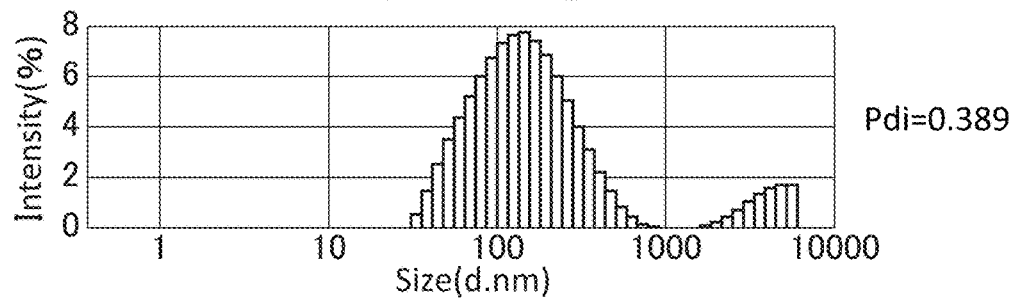
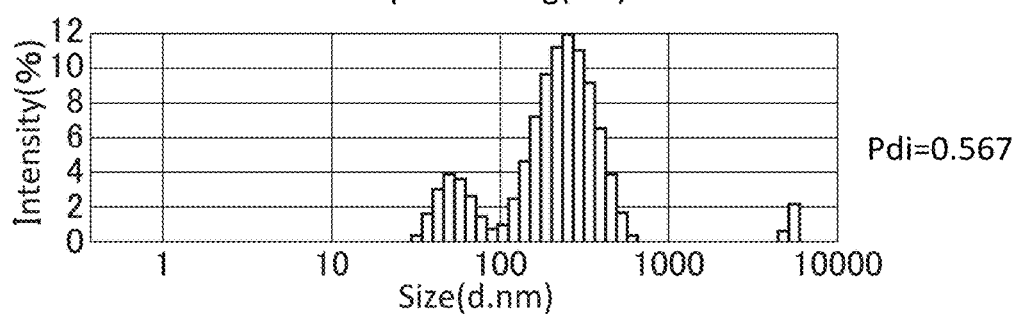

FIG. 3
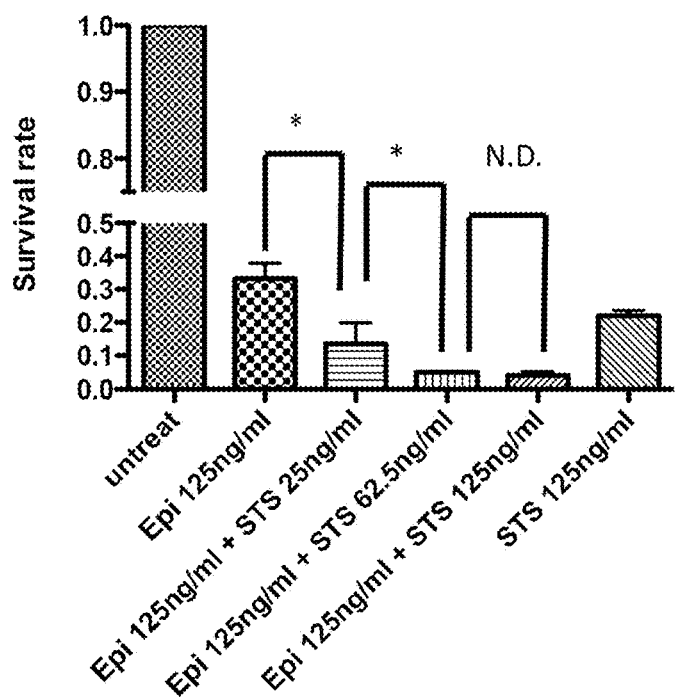
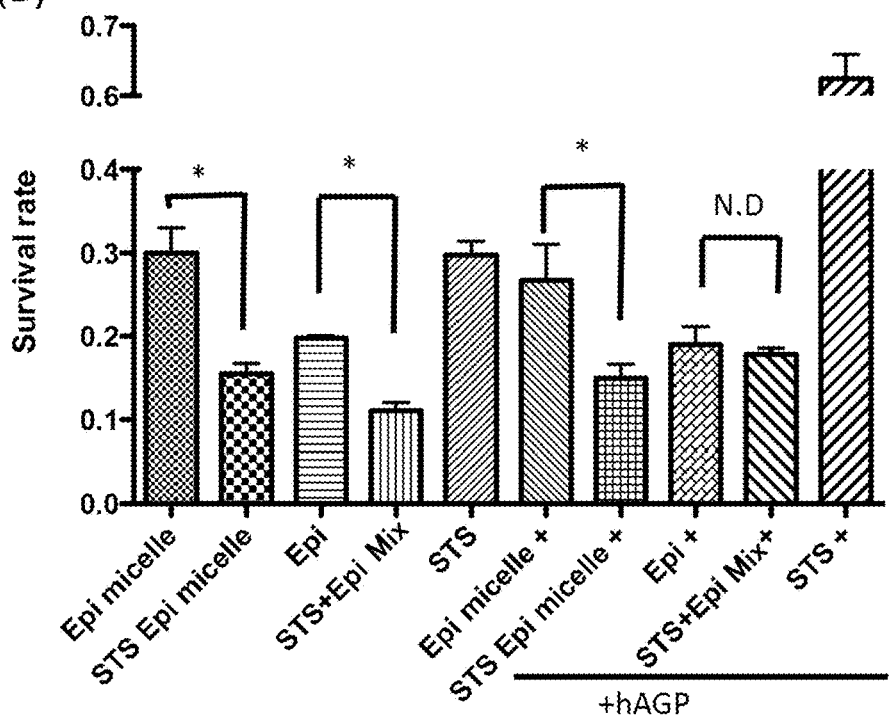

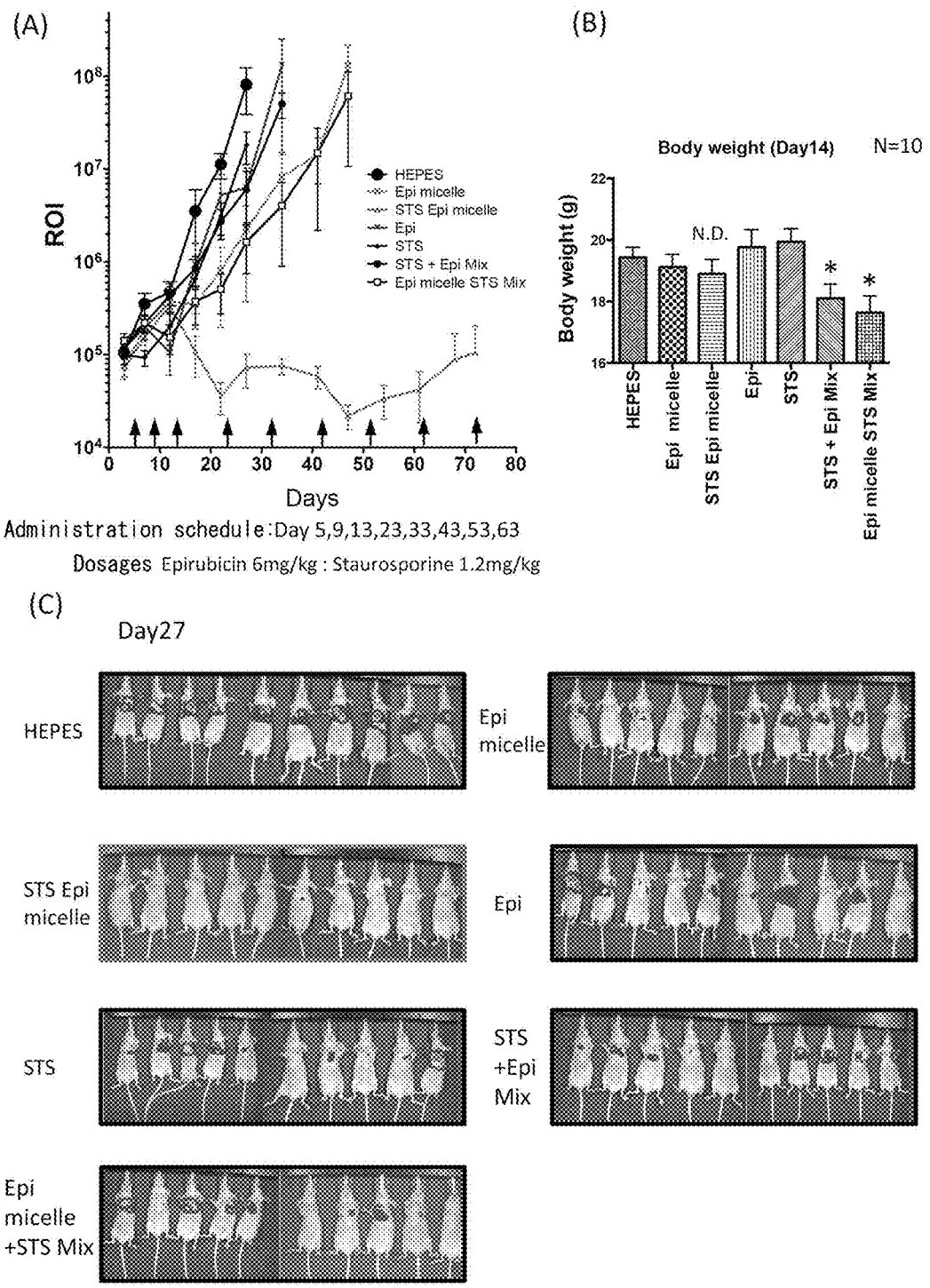
FIG. 6A-C

FIG. 9
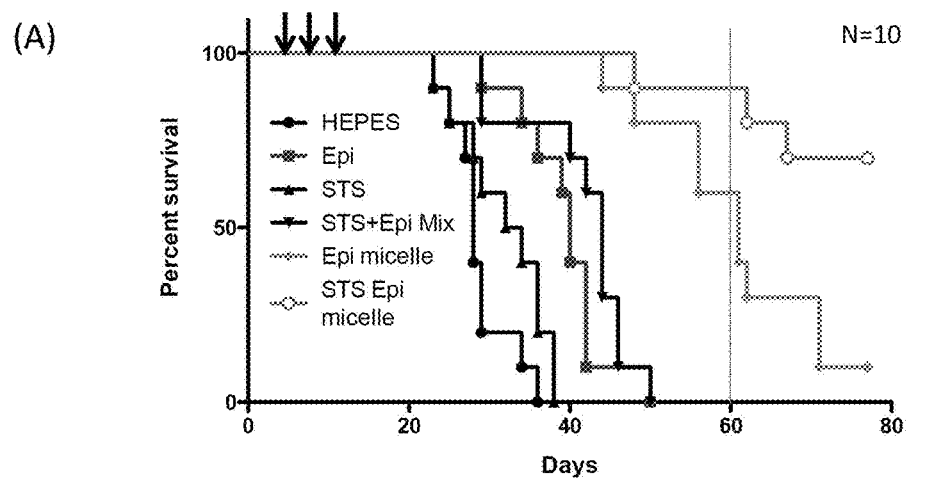
(A)
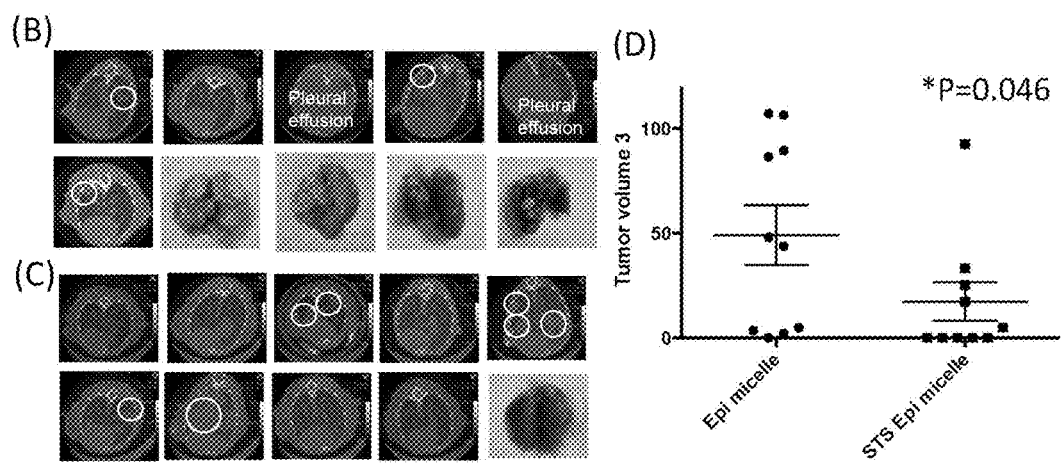
(B) (C) (D)
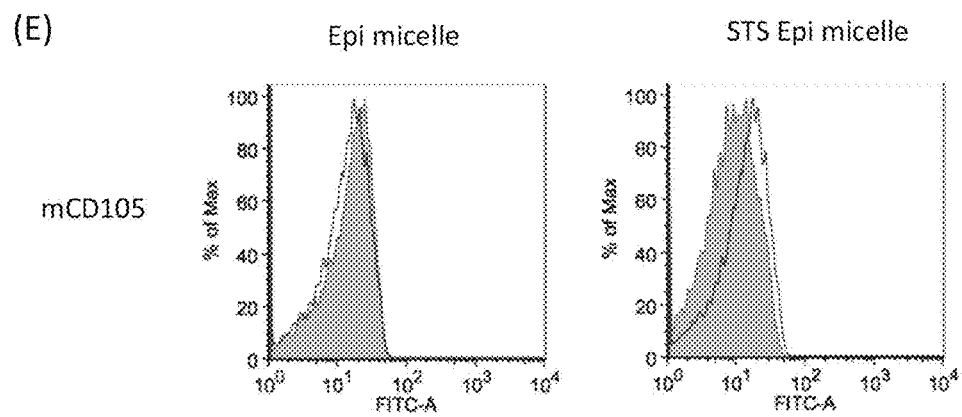
(E) Epi micelle     STS Epi micelle
mCD105

FIG. 12
(A)
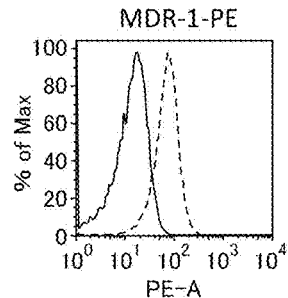
(B)
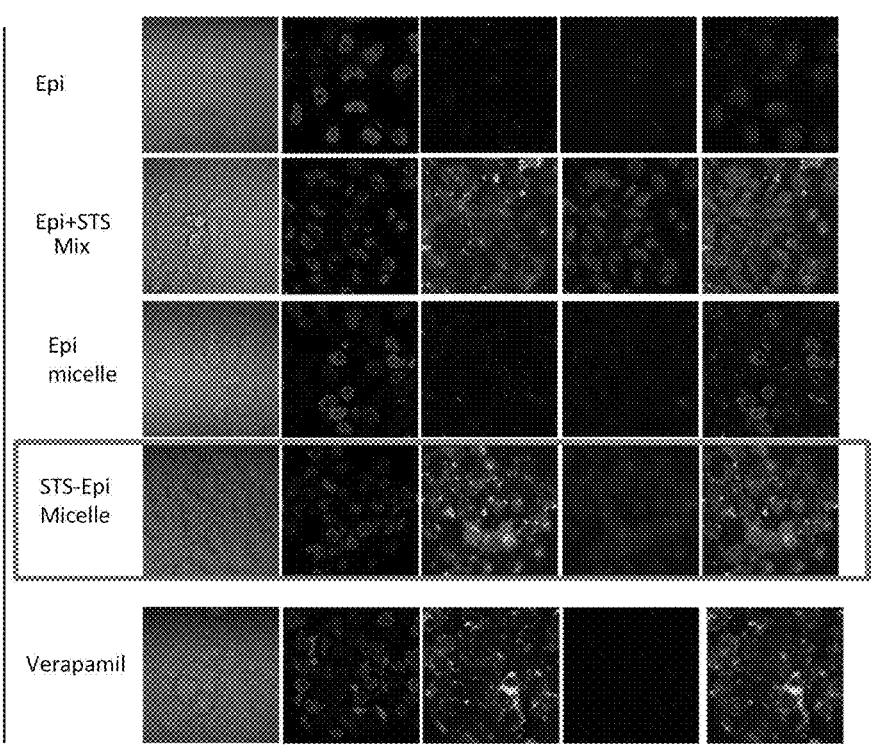

FIG. 13
(A)
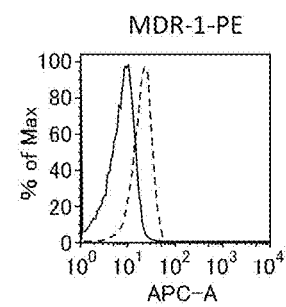
(B)
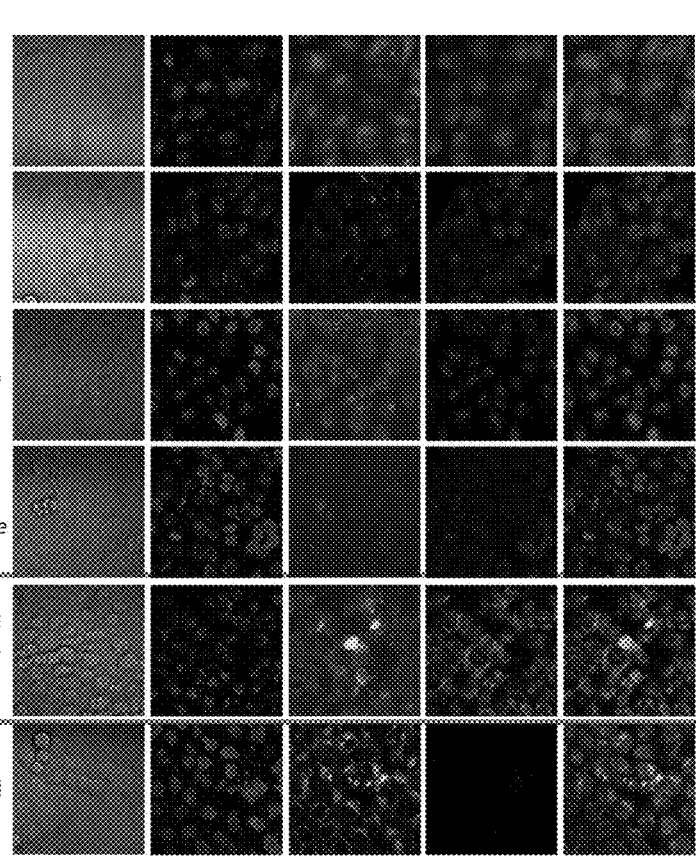

FIG. 14A-C
(A) Mesothelioma MSTO-211H EPI-R
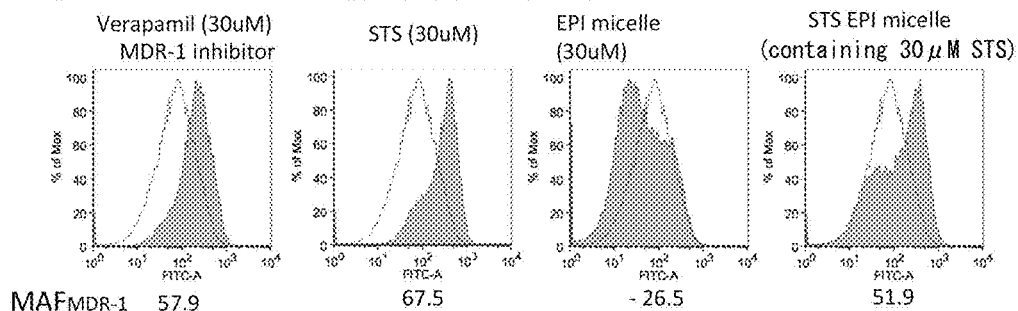
(B) Breast cancer MCF-7 EPI-R
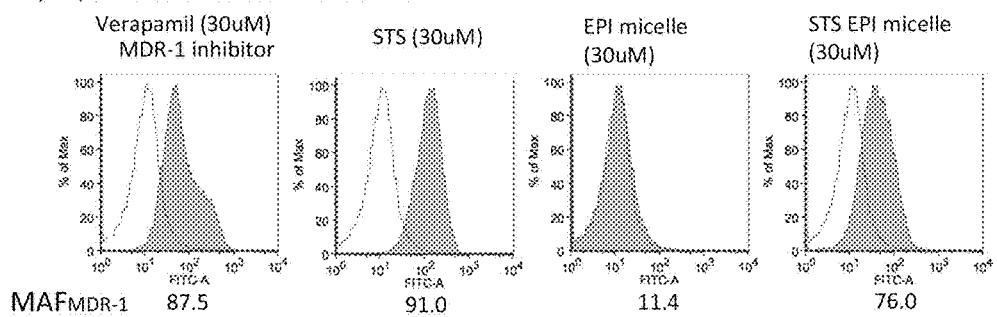
(C) Lung cancer H460 Cis-R
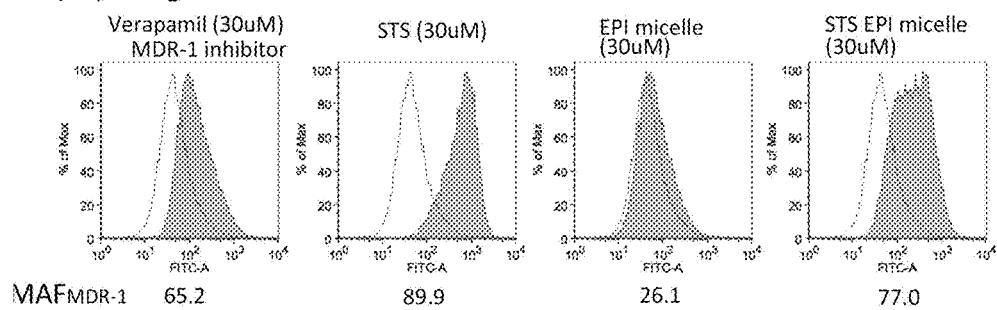

FIG. 14D-E
(D) BCRP Highly Expressing Cancer (Hela)
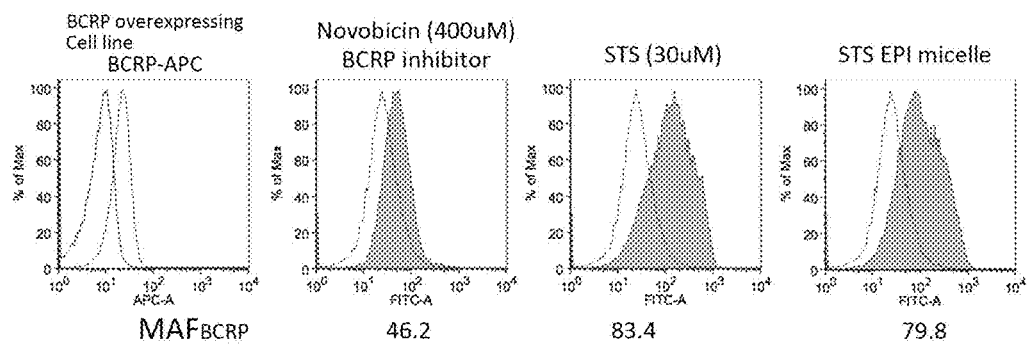
(E) MRP Highly Expressing Cancer (A549)
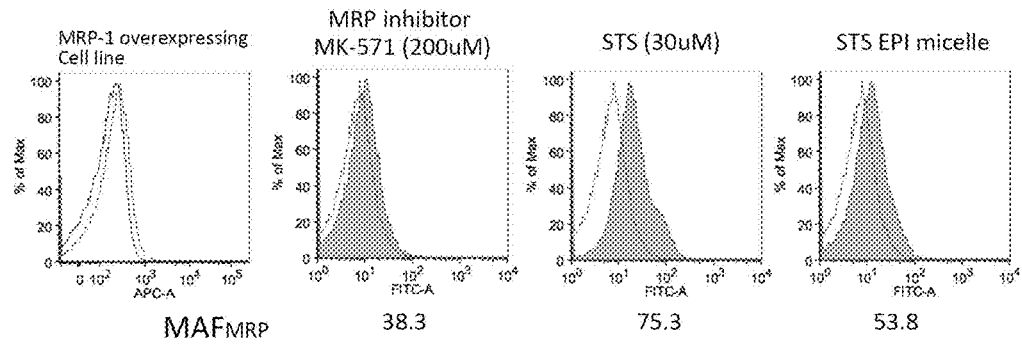

MICELLE CONTAINING EPIRUBICIN-COMPLEXED BLOCK COPOLYMER AND ANTI-CANCER AGENT, AND PHARMACEUTICAL COMPOSITION CONTAINING SAID MICELLE APPLICABLE TO TREATMENT OF CANCER, RESISTANT CANCER OR METASTATIC CANCER

TECHNICAL FIELD

The present invention relates to a micelle comprising an epirubicin-conjugated block copolymer and anti-cancer agent, a method for producing said micelle, and a pharmaceutical composition comprising said micelle.

BACKGROUND ART

When a drug is administered systemically to an individual either orally or by intravenous injection and the like, there are cases in which adverse side effects are observed in normal tissue other than the targeted lesion, thereby forcing modification or discontinuation of the treatment method. In addition, depending on the particular drug, there are some cases that it may also be difficult to maintain the concentration of a drug that allows that drug to be effective, and that the drug may be metabolized prior to being delivered to the target site.

In order to solve these problems, sophisticated pharmaceutical techniques and concepts have been introduced that attempt to optimize therapeutic efficacy by imparting a desirable drug concentration-time pattern at the target site of action by controlling the pharmacokinetics of the drug in the body or by selective delivery thereof, and extensive research is currently being conducted in this field. These techniques and concepts are collectively referred to as a drug delivery system (DDS), and have recently come to be viewed with particular importance from the viewpoint of delivering substances such as anti-cancer drugs, DNA or peptides to the site of a tumor, inflamed site or other lesion with greater safety and efficiency.

Specific examples of methods for deploying DDS that have been developed include methods utilizing drug carriers such as liposomes, emulsions or nanoparticles, methods containing drugs in high molecular weight carriers such as polymeric micelles, and methods covalently bonding drugs to synthetic polymers or naturally occurring polysaccharides. The development of DDS preparations makes it possible to achieve superior efficacy and reduced adverse side effects for compounds that have already been developed as drugs. In addition, the use of DDS is expected to revive drugs, for which development had been abandoned from the viewpoints of adverse side effect or other factors, for use as pharmaceuticals. However, various issues must still be addressed when attempting to use these systems at the practical level, and among these, avoidance of the body's foreign substance recognition system, increasing drug concentration in DDS drug carriers, and control of drug release rate are considered to be particularly important.

With respect to avoiding the body's foreign substance recognition system, coating the surface of liposomes and other drug carriers with a hydrophilic polymer such as polyethylene glycol has made it possible to prevent adsorption by plasma proteins and opsonin proteins and enhance stability in the blood, thereby avoiding capture in the liver and spleen by the reticuloendothelial system (RES). As a result, liposomes and polymeric micelles allow the obtaining of high blood retention levels following intravenous administration and are able passively accumulate in tumor tissue, inflamed sites and other tissues having increased vascular permeability, thereby enabling treatment to be carried out efficiently.

On the other hand, with respect to drug content in DDS drug carriers, a higher drug content makes it possible to reduce the amount of carrier required to deliver the required drug, and as a result thereof, is advantageous in terms of both therapeutic efficacy and pharmaceutical design (J. Med. Chem., 45, 4336-4343 (2002) (NPL1)). Nevertheless, there are limitations on the drug content of liposomes and polymeric micelles from the viewpoint of physical stability, and if the drug content is increased in polymer complex types of drug carriers, the increase has an effect on the properties of the water-soluble polymer and the water-solubility thereof ends up decreasing. As a result, since interactions with plasma components are no longer able to be inhibited and it is no longer possible to maintain retention in the blood, nearly all such carriers have a drug content of only several percent (CRIPS 5(2), 2-8 (2004) (NPL2)). Research has been conducted with the goal of achieving both high drug content and superior blood retention, and DDS compounds are being developed that have a high drug content and superior blood retention.

In addition, with respect to drug release, a system in which a drug is stably incorporated or bound to a carrier in the blood and is then rapidly released after having arrived at diseased tissue is ideal from the viewpoints of reducing adverse side effects and enhancing therapeutic efficacy. Various types of environment-sensitive carriers, or in other words, drug carriers that undergo a change in their physical properties in response to an environmental change induced by a lesion or in response to a difference between the environments of normal tissue and the site of a lesion, are being examined in order to realize a higher level of drug release control.

For example, HPMA copolymer-doxorubicin (PK1) has been reported that couples doxorubicin to an HPMA polymer having a molecular weight of about 30,000 Da through a spacer. Although PK1 allows the drug to be released by cathepsin B, which is more highly expressed at the site of a tumor than normal tissue, the drug content thereof is only about 8.5%, preventing it from achieving a high drug content.

On the other hand, since the local pH at the site of a tumor, inflammation or other diseased site is lower than that of normal tissue, studies have been conducted that utilize this phenomenon for the purpose of allowing a drug to be released in response to the environment attributable to such a change in pH at the diseased site (Adv. Drug Delivery Rev., 56, 1023-1050 (2004) (NPL3); Biochim. Biophys. Acta., 1329(2), 291-320 (1997) (NPL4)).

In addition, polymer complexes responding to a low pH environment within cells (J. Controlled Release, 87, 33-47 (2003) (NPL5)) and polymeric micelles (Bioconjugate Chem., 16, 122-130 (2005) (NPL6); J. Controlled Release, 64, 143-153 (2000) (NPL7)) have been reported in which a drug is released in precise response to a low pH environment within endosomes after having been locally incorporated into individual cancer cells of a tumor via the endocytosis pathway. Moreover, biodegradable doxorubicin micelles (J. Controlled Release, 96, 273-283 (2004) (NPL8)) and adriamycin (Bioconjugate Chem., 18, 1131-1139 (2007) (NPL9)) have been reported that are designed to be selectively incorporated in cancer cells highly expressing folic acid receptors by coupling folic acid to PEG expressed on the surface of polymeric micelles. Moreover, attempts have also been made to increase blood retention, and polymeric micelles have been developed that satisfy all of the conditions of pH dependency of drug release, superior retention in the blood and high drug content (Japanese Patent No. 4791435 (PTL1); US Patent No. 2008/0248097 (PTL2)).

However, when treatment is performed using anti-cancer agents, although elimination of the cancer can be temporarily confirmed, currently developed anti-cancer agents are unable to completely eradicate all cancer cells, and cancer is known to recur and metastasize due to the survival of an extremely small number of cancer cells that have acquired resistance. In particular, these cancer cells that have acquired resistance have been reported to include self-replicating and pluripotent cells referred to as cancer stem cells (Nat. Med., 3, 730-737 (1997) (NPL10); Nat. Med., March 17(3), 313-319 (2011) (NPL11)). Cancer has been clearly demonstrated to occur in and progress from cancer stem cells in several types of cancer including acute myelogenous leukemia. Since the development of anti-cancer drugs targeted at reducing the size of solid tumors alone is inadequate for these cancers, there is a desire for the development of an anti-cancer agent that is capable of eradicating cancer stem cells.

PRIOR ART DOCUMENTS

Patent Literature

PTL1: Japanese Patent No. 4781435
PTL2: U.S. Patent No. 2008/0248097

Non-Patent Literature

NPL1: J. Med. Chem., 45, 4336-4343 (2002)
NPL2: CRIPS 5(2), 2-8 (2004)
NPL3: Adv. Drug Delivery Rev., 56, 1023-1050 (2004)
NPL4: Biochim. Biophys. Acta., 1329(2), 291-320 (1997)
NPL5: J. Controlled Release, 87, 33-47 (2003)
NPL6: Bioconjugate Chem., 16, 122-130 (2005)
NPL7: J. Controlled Release, 64, 143-153 (2000)
NPL8: J. Controlled Release, 96, 273-283 (2004)
NPL9: Bioconjugate Chem., 18, 1131-1139 (2007)
NPL10: Nat. Med., 3, 730-737 (1997)
NPL11: Nat. Med., March 17(3), 313-319 (2011)
NPL12: Biochemistry, 40, 2564-2571 (2001)
NPL13: British Journal of Cancer, 73, 1063-1068 (1996)
NPL14: Cancer Research, 64, 1242-1246, Feb. 15, 2004

DISCLOSURE OF THE INVENTION

Technical Problem

An object of the present invention is to provide a pharmaceutical that is able to solve the aforementioned problems. More specifically, an object of the present invention is to develop a pharmaceutical that demonstrates therapeutic efficacy against drug-resistant tumors.

Solution to Problem

As a result of conducting extensive studies to solve the aforementioned problems, the inventors of the present invention found that a micelle comprising an anti-cancer agent inside the core of a micelle formed by an epirubicin-conjugated copolymer demonstrates therapeutic efficacy against epirubicin-resistant tumors, thereby leading to completion of the present invention. Thus, the present invention relates to the inventions indicated below.

[1] A pH-sensitive micelle comprising a compound which is an anti-cancer agent and an epirubicin-conjugated copolymer, in which epirubicin or a salt thereof is bound to a block copolymer represented by the following Chemical Formula (I) or Chemical Formula (II) via hydrazide groups of the block copolymer, and wherein as a result of binding epirubicin or salt thereof, is in a state in which units having a hydrazide group in a side chain thereof account for more than 0% to no more than 35% of the total number of polyamino acid units in the block copolymer:

[Chemical Formula 1]

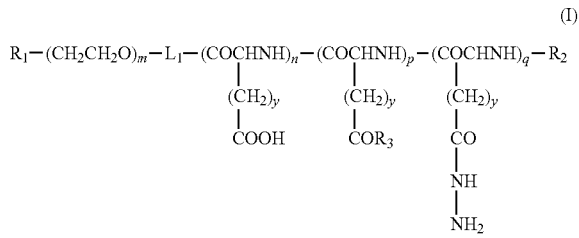

or

[Chemical Formula 2]

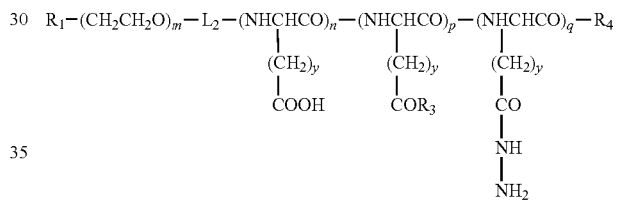

(wherein, $R_1$, which may be the same or different, represents a hydrogen atom, methoxy group, methyl group, substituted linear, branched or cyclic $C_1$-$C_{12}$ alkyl group, and the substituent thereof is a functional group selected from the group consisting of amaleimido group, amino group, carboxyl group, thiol group, hydroxyl group and active ester group, which may be protected, $R_2$ represents a hydrogen atom, saturated or unsaturated $C_1$-$C_{30}$ aliphatic carbonyl group or arylcarbonyl group, $R_3$ represents —O—$R_5$ or —NH—$R_5$, and $R_5$, which may be the same or different, represents a hydrophobic group, $R_4$ represents a hydroxyl group, saturated or unsaturated $C_1$-$C_{30}$ aliphatic oxy group or aryl-lower alkyloxy group, $L_1$ and $L_2$ independently from each other represent a linker, m represents an integer of 5 to 1000,
n represents an integer of 0 to 1000,
p represents an integer of 1 to 1000,
q represents an integer of 1 to 1000, provided that in the case units having a hydrophobic group in a side chain thereof account for 25% to 75% of the total number of polyamino acid units in the block copolymer and units having a carboxylic acid are present in a side chain thereof, units having a carboxylic acid group in a side chain thereof, units having a hydrophobic group in a side chain thereof and units having a hydrazide group in a side chain thereof are randomly distributed throughout the entire polyamino acid region, while in the case units having a carboxylic acid group in a side chain thereof are not present, units having a hydrophobic group in a side chain thereof and units having a hydrazide group in a side chain thereof are randomly distributed throughout the entire polyamino acid region, and y represents an integer of 1 or 2).

[2] The micelle described in [1], wherein the compound which is an anti-cancer agent acts on cancer stem cells.

[3] The micelle described in [1] or [2], wherein $R_5$ is a hydrophobic group selected from the group consisting of a benzyl group, phenyl group, $C_4$-phenyl group and $C_8$-$C_{16}$ alkyl group.

[4] The micelle described in any two of [1] to [3], wherein epirubicin is bound to hydrazide groups at a number equal to 10% to 50% of the total number of polyamino acid units.

[5] The micelle described in [4], wherein epirubicin is bound to hydrazide groups at a number equal to 10% to 40% of the total number of polyamino acid units.

[6] The micelle described in any one of [1] to [5], wherein the anti-cancer agent is selected from the group consisting of a compound having an indolocarbazole backbone, afatinib, axitinib, bosutinib, canertinib, cediranib, crizotinib, dasatinib, dabrafenib, danusertib, erlotinib, gefitinib, imatinib, lapatinib, nilotinib, pazopanib, ponatinib, regorafenib, sorafenib, sunitinib, tandutinib, tofacitinib, vandetanib and vemurafenib.

[7] The micelle described in [6], wherein the compound having an indolocarbazole backbone is a compound represented by the following formula:

[Chemical Formula 3]

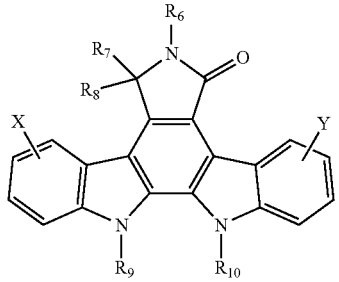

(wherein,

X and Y independently represent H, OH, Cl, a propoxy group or ethylthiomethyl group, $R_6$ represents H, a $C_{1-3}$ alkyl group, —$NH_2$, benzyl group,

[Chemical Formula 4]

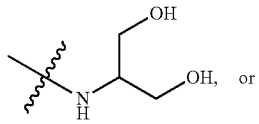

, or

[Chemical Formula 5]

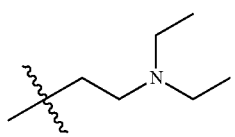

$R_7$ and $R_8$ independently from each other represent H, —OH or a methoxy group, or together with each other form O=, $R_9$ and $R_{10}$ respectively represent a hydrogen atom, methyl group, β-D-glucopyranosyl group, 4-O-methyl-β-D-glucopyranosyl group, cyanoethyl group, or

[Chemical Formula 6]

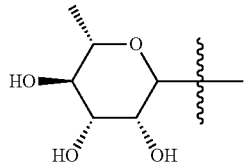

or together with each other form

[Chemical Formula 7]

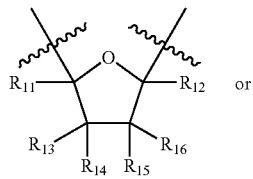  or

[Chemical Formula 8]

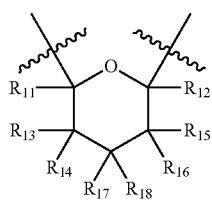

wherein $R_{11}$ represents a methyl group, $R_{12}$ represents H, $R_{13}$ and $R_{14}$ independently from each other represent H, a methoxy group, —OH, a hydroxymethyl group, methylcarboxylate group, methylamino group, methylaminomethyl group, propylaminomethyl group, dimethylaminomethyl group or

[Chemical Formula 9]

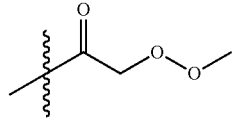

$R_{15}$ and $R_{16}$ independently from each other represent H, OH or

[Chemical Formula 10]

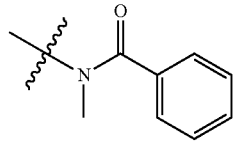

and, $R_{17}$ and $R_{18}$ represent H, OH, methylamino groups, dimethylamino groups, oxime groups.

[Chemical Formula 11]

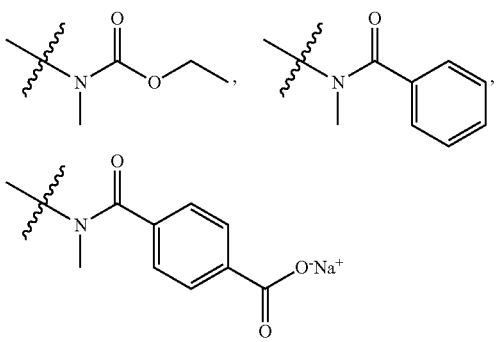

[8] The micelle described in [6], wherein the compound having an indolocarbazole backbone is at least one compound selected from the group consisting of staurosporine, 7-hydroxystaurosporine, KT5926, staurosporine aglycone, SF2370, KT5823, 4'-N-benzoylstaurosporine, PKC412, Go6976, N,N-dimethylstaurosporine, NA 0359, N-ethoxycarbonyl-7-oxostaurosporine, KT-6124, CGP42700, 4'-demethylamino-4',5'-dihydroxystaurosporine, 7-oxostaurosporine, CEP751, NA0346, NA0359, 3'-demethoxy-3'-hydroxystaurosporine, KT 6006, 7-O-methyl-UCN 01, TAN 999, NA 0346, NA 0345, NA 0344, CGP44171A, SCH 47112, N,N-dimethylstaurosporine, TAN 1030A, lestaurtinib, 4'-demethylamino-4'-hydroxystaurosporine, AFN941, edotecarin, becatecarin, and salts thereof.

[9] The micelle described in [8], wherein the compound having an indolocarbazole backbone is at least one compound selected from the group consisting of staurosporine, 7-hydroxystaurosporine, PKC412 and lestaurtinib.

[10] The micelle described in any one of [1] to [9], wherein the weight ratio of the epirubicin-conjugated copolymer and the anti-cancer agent is 5:2 to 10:1.

[11] A pharmaceutical composition for treating cancer or a tumor, comprising the micelle described in any one of [1] to [10].

[12] The pharmaceutical composition described in [11], wherein the cancer or tumor is selected from the group consisting of neuroblastoma, liver cancer, malignant melanoma, uterine cancer, bladder cancer, bile duct cancer, esophageal cancer, osteosarcoma, testicular tumor, thyroid cancer, acute myelogenous leukemia, brain tumor, prostate cancer, pancreatic cancer, head and neck squamous cell carcinoma, mesothelioma, lung cancer, colon cancer, kidney cancer, ovarian cancer and breast cancer.

[13] The composition described in [11], which is effective against cancer or tumors containing cancer stem cells.

[14] The composition described in [12], wherein the cancer or tumor containing cancer stem cells is at least one cancer selected from the group consisting of acute myelogenous leukemia, brain tumor, prostate cancer, pancreatic cancer, head and neck squamous cell carcinoma, mesothelioma, lung cancer, colon cancer, kidney cancer, ovarian cancer and breast cancer.

[15] A method for treating cancer, comprising administering an effective amount of the micelle described in any one of [1] to [10].

[16] A use of the micelle described in any one of [1] to [10] for producing a pharmaceutical for the treatment of cancer.

[17] The micelle described in any one of [1] to [9] for the treatment of cancer.

Effects of the Invention

The micelle of the present invention has therapeutic efficacy against cancer or tumors that is superior to micelles formed from an epirubicin-conjugated block copolymer. A micelle incorporating an anti-cancer agent is able to release epirubicin and an anti-cancer agent at the site of cancer or a tumor. In addition, in the case of using an ABC transporter inhibitor as an anti-cancer agent, the efficacy of epirubicin is enhanced since the drug efflux mechanism is inhibited in cancer or a tumor.

BRIEF DESCRIPTION OF THE DRAWINGS

FIG. 1 is a drawing indicating the incorporation of compounds in micelles of an epirubicin-conjugated block copolymer along with structural formulas of the incorporated compounds. FIG. 1A is a drawing indicating the structural formula of an epirubicin-conjugated block copolymer along with the particle size and polydispersity index (PDI) of micelles formed by this copolymer as determined by dynamic light scattering using a Zetasizer. FIGS. 1B and 1C indicate the structural formulas of staurosporine and UCN-01, respectively, along with the particle size and PDI as determined by dynamic light scattering using a Zetasizer when incorporating in micelles formed by an epirubicin-conjugated block copolymer.

FIG. 1 is a drawing indicating the incorporation of compounds in micelles of an epirubicin-conjugated block copolymer along with the structural formulas of the incorporated compounds. FIGS. 1D to 1F respectively indicate the structural formulas of reserpine, lestaurtinib and PKC412 along with the particle size and PDI as determined by dynamic light scattering using a Zetasizer when incorporating in micelles formed by an epirubicin-conjugated block copolymer.

FIG. 1G indicates the particle size and PDI as determined by dynamic light scattering using a Zetasizer in the case of changing the concentration ratio of each compound when incorporating staurosporine in micelles of an epirubicin-conjugated block copolymer.

FIG. 2C indicates changes in the survival rate with respect to MSTO-211H measured according to in vitro anti-cancer activity of a pH-sensitive epirubicin micelle (Epi micelle), staurosporine-incorporating, pH-sensitive epirubicin micelle (STS Epi micelle pH) and staurosporine-incorporating, pH non-sensitive epirubicin micelle (STS Epi micelle (amide)). FIG. 2D indicates changes in tumor volume as determined by luminescence in the case of administering a pH-sensitive epirubicin micelle (Epi micelle), staurosporine-incorporating, pH-sensitive epirubicin micelle (STS Epi micelle pH) and staurosporine-incorporating, pH non-sensitive epirubicin micelle (STS Epi micelle (amide)) into model mice orthotopically implanted with MSTO-211 mesothelioma expressing luciferase gene.

FIG. 3A is a drawing showing the synergistic effects demonstrated by combining an epirubicin micelle with staurosporine. FIG. 3B is a drawing indicating that, although the effect of staurosporine is diminished as a result of bonding with al-acid glycoprotein in the blood, it is no longer affected by al-acid protein in the case of being incorporated in an epirubicin micelle.

FIG. 4A indicates the results of FACS of cells inducing annexin V-positive apoptosis in the case of having added the aforementioned drugs to epirubicin-resistant mesothelioma (MSTO-211H) and breast cancer (MCF-7) cells, while FIG. 4B indicates graphs of those results. FIG. 4C depicts graphs indicating the effects of an epirubicin micelle (Epi micelle) and staurosporine-incorporating epirubicin micelle (STS Epi micelle) on mesothelioma (MSTO-211H) cells and epirubicin-resistant mesothelioma (MSTO-211H-EPI-R) cells. FIG. 4D depicts graphs indicating the effects of an epirubicin micelle (Epi micelle) and staurosporine-incorporating epirubicin micelle (STS Epi micelle) on breast cancer (MCF-7) cells and epirubicin-resistant breast cancer (MCF-7-EPI-R) cells.

FIG. 6 indicates changes in fluorescence intensity of luciferase in the case of having intravenously administered an epirubicin micelle (Epi micelle), staurosporine-incorporating epirubicin micelle (STS Epi micelle), epirubicin (Epi), staurosporine (STS), a mixture of staurosporine and epirubicin (STS+Epi Mix) and a mixture of epirubicin micelle and staurosporine (Epi micelle STS Mix) in an orthotopic model of metastasis obtained by transplanting an epirubicin-resistant malignant mesothelioma strain genetically expressing luciferase into the thymus (FIG. 6A), while FIG. 6B indicates changes in body weight during the experimental period, and FIG. 6C indicates the appearance of the luminescence of luciferase on Day 27.

FIG. 7B indicates the effects of a staurosporine-incorporating epirubicin micelle on other cancer stem cell markers CD44v10 and CD133. FIG. 7C indicates changes in tumor volume in the case of having intravenously administered an epirubicin micelle (Epi micelle), epirubicin (Epi), mixture of staurosporine and epirubicin (STS+Epi Mix), staurosporine-incorporating epirubicin micelle (STS Epi micelle) and mixture of staurosporine and epirubicin micelle (Epi micelle STS Mix) in colon cancer.

FIG. 9 indicates survival curves in the case of having intravenously administered epirubicin (Epi), staurosporine (STS), mixture of staurosporine and epirubicin (STS+Epi Mix), epirubicin micelle (Epi micelle) and staurosporine-incorporating epirubicin micelle (STS Epi micelle) for kidney cancer and metastatic lung cancer in an orthotopic model to which mouse kidney cancer (Renca) is transplanted into the kidneys (FIG. 9A), CT images of the lung taken at 60 days after administration of the epirubicin micelle, or photographs taken at biopsy in the case of death (FIG. 9B), and CT images taken at 60 days after administration of the staurosporine-incorporating epirubicin micelle, or photographs taken at biopsy in the case of death (FIG. 9C). Metastatic cancer was observed at those locations indicated with circles, and exudation of ascites was observed in two cases shown in FIG. 9B. FIG. 9D is a graph comparing tumor volume on Day 60 after transplant or at the time of death. FIG. 9E depicts graphs indicating that the level of a kidney cancer stem cell marker in the form of mouse CD105 was decreased by staurosporine-incorporating epirubicin micelle.

FIG. 11B depicts graphs of the results of FIG. 11A.

FIG. 12A is a graph indicating changes in expression of MDR-1, which is one of ABC transporters, before and after acquisition of epirubicin resistance in breast cancer cells (MCF-7). FIG. 12B depicts photographs comparing elimination of epirubicin and eFluxx-ID outside the cells in breast cancer (MCF-7) cells not having acquired epirubicin resistance (original cells) and breast cancer (MCF-7) cells having acquired epirubicin resistance (epirubicin-resistant strain). Although epirubicin and eFlux-ID were eliminated outside cells of the epirubicin-resistant strain in the case of administration of epirubicin or epirubicin micelle alone, as a result of using a mixture of staurosporine and epirubicin or a staurosporine-incorporating epirubicin micelle, epirubicin and eFlux-ID were not eliminated outside the cells, but rather were shown to remain within the cells.

FIG. 13A is a graph indicating changes in expression of MDR-1, which is one of ABC transporters, before and after acquisition of cisplatin resistance in lung cancer cells (H460). FIG. 13B depicts photographs comparing elimination of epirubicin and eFlux-ID outside the cells in lung cancer (H460) cells not having acquired cisplatin resistance (original cells) and lung cancer (H460) cells having acquired epirubicin resistance (cisplatin-resistant strain). Although epirubicin and eFlux-ID were eliminated outside cells of the cisplatin-resistant strain in the case of administration of epirubicin or epirubicin micelle alone, as a result of using a mixture of staurosporine and epirubicin or a staurosporine-incorporating epirubicin micelle, epirubicin and eFlux-ID were not eliminated outside the cells, but rather were shown to remain within the cells.

FIG. 14 indicates that staurosporine and staurosporine-epirubicin micelle prevented elimination of each of the drugs shown in cells resistant to each drug and cells highly expressing ABC transporter, and MAF values are indicated below the graphs. Epirubicin-resistant mesothelioma cells (MSTO-211H EPI-R) are used in FIG. 14A, epirubicin-resistant breast cancer cells (MCF-7 EPI-R) are used in FIG. 14B, and cisplatin-resistant lung cancer cells (H460 Cis-R) are used in FIG. 14C.

FIG. 14D-E Hela cells highly expressing BCRP, which is one of ABC transporters, are used in FIG. 14D, and A549 cells highly expressing MRP, which is one of ABC transporters, are used in FIG. 14E.

BEST MODE FOR CARRYING OUT THE INVENTION

Figure 2:
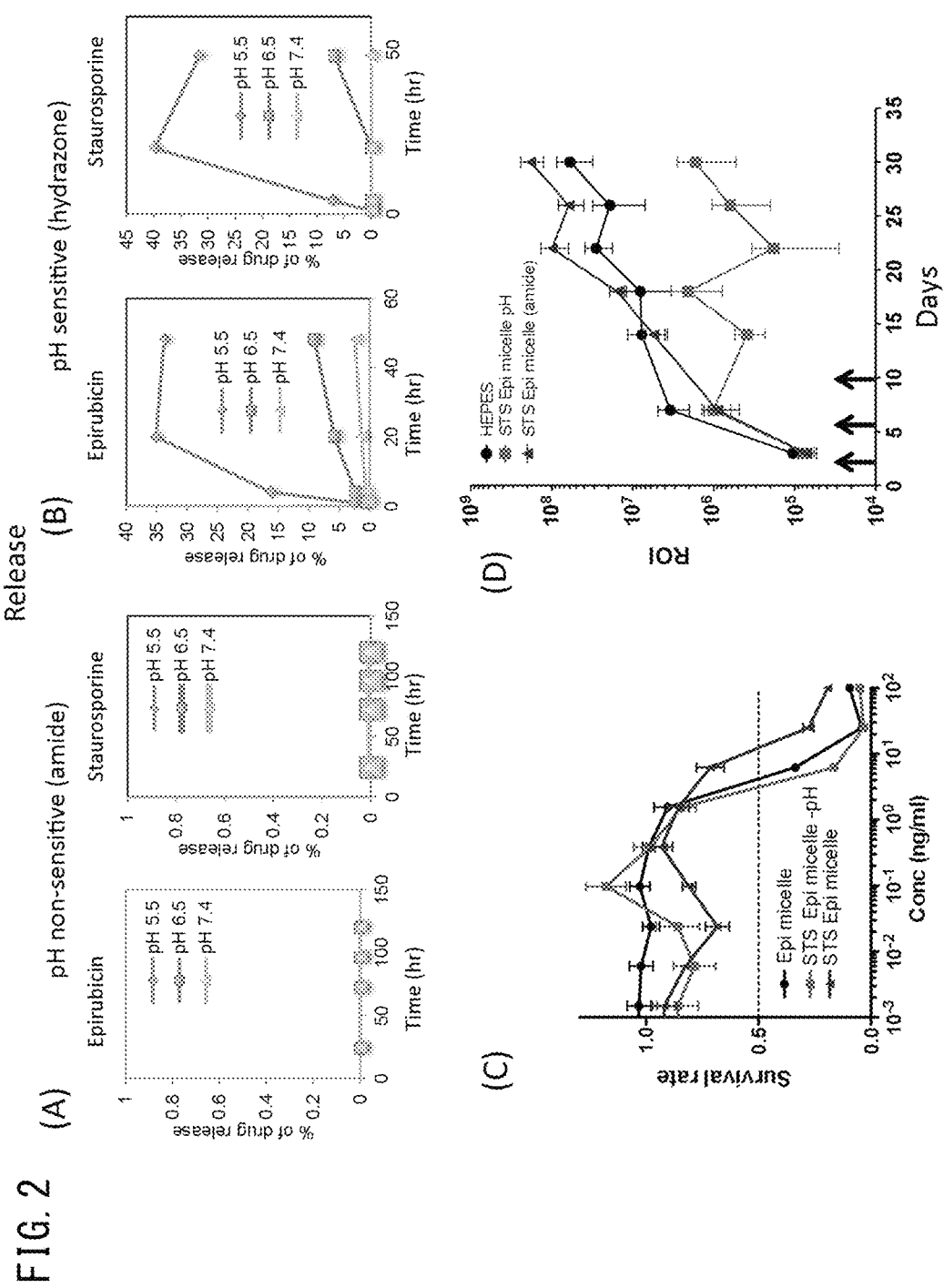
FIG. 2 is a drawing indicating the respective pH-sensitive release characteristics of staurosporine and epirubicin from staurosporine-incorporating epirubicin micelles. pH-sensitive release characteristics were not observed for both epirubicin and staurosporine in epirubicin-conjugated micelles in which epirubicin is bound to a block copolymer via amide bonds (FIG. 2A). On the other hand, pH-sensitive release characteristics were observed for both epirubicin and staurosporine in epirubicin-conjugated micelles in which epirubicin is bound to a block copolymer via hydrazone bonds (FIG. 2B).

In one embodiment thereof, the present invention relates to a micelle comprising an epirubicin-conjugated block copolymer and an anti-cancer agent, which is different from epirubicin. More specifically, the micelle of the present invention has an anti-cancer agent arranged inside the core of a micelle formed by an epirubicin-conjugated block copolymer. The anti-cancer drug demonstrates action against cancer stem cells, and is an anti-cancer stem cell agent, anti-cancer stem cell suppressor or anti-cancer stem cell inhibitor.

The epirubicin-conjugated block copolymer in the present invention contains a block copolymer for incorporating a drug, containing a water-soluble polymeric region composed of polyethylene glycol and a polyamino acid region having a hydrazide group and hydrophobic group in a side chain thereof, and epirubicin bound to the block copolymer via the hydrazide group of said block copolymer. The epirubicin-conjugated block copolymer is able to form a polymeric micelle which arranges the water-soluble polymeric region at the outer shell and arranges the hydrophobic polyamino acid region at the inner core, and epirubicin is arranged in the inner core. The anti-cancer agent is arranged in the inner core together with epirubicin as a result of interacting with epirubicin. A micelle of an epirubicin-conjugated block copolymer having an anti-cancer drug arranged within the core thereof can be said to be an anti-cancer agent-incorporating epirubicin micelle, wherein an ABC transporter inhibitor can be incorporated as an anti-cancer. In the case an indolocarbazole compound is incorporated as the ABC transporter inhibitor, the resulting micelle can be said to be an indolocarbazole compound-incorporating epirubicin micelle. Moreover, in the case the indolocarbazole compound is staurosporine, the resulting micelle can be said to be a staurosporine-incorporating epirubicin micelle.

In the epirubicin-conjugated block copolymer, the epirubicin is conjugated to the block copolymer due to dehydration condensation of the ketone structure of epirubicin and hydrazide groups of the block copolymer (FIG. 1A). Epirubicin is bound to the block copolymer through a hydrazone structure and the hydrazone is subjected to hydrolysis at low pH. Therefore, when the micelle which is formed from the epirubicin conjugated block copolymer is placed under acidic environment which is generated at a location of inflammation or other diseased site, such as at pH of 3.0 to 6.5, the epirubicin is released and is able to demonstrate anti-cancer activity at the diseased site. The anti-cancer agent arranged inside the core is also released at the time of release of epirubicin from the micelle of the present invention. In this manner, a micelle in which the hydrazone structure of an epirubicin-conjugated block copolymer is degraded in an acidic environment enabling the release of epirubicin or epirubicin and an anti-cancer agent can be referred to as a pH-sensitive micelle. The use of a pH-sensitive micelle makes it possible to deliver an anti-cancer agent, which ends up losing activity in the blood due to the hydrophobicity thereof or the binding activity to blood proteins, to a target tissue or diseased site while retaining the activity thereof, thereby enabling tissue-specific or site-specific demonstration of the superior activity of the anti-cancer agent.

The block copolymer for incorporating a drug according to the present invention can be prepared by introducing a hydrazide group and hydrophobic group into a block copolymer composed of a water-soluble polymeric region consisting of polyethylene glycol and a polyamino acid region.

Examples of the block copolymer that can be produced particularly easily and used favorably in the present invention include those represented by the following formulas (I) and (II):

[Chemical Formula 12]

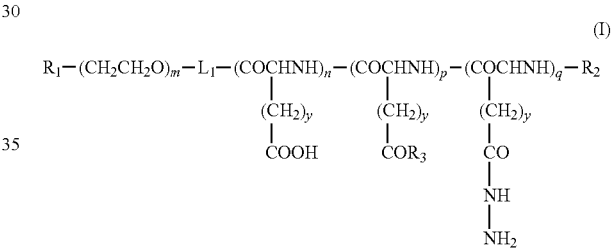

or

[Chemical Formula 13]

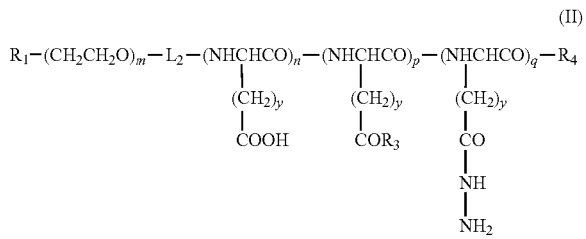

(wherein, $R_1$, which may be the same or different, represents a hydrogen atom, methoxy group, methyl group, substituted linear, branched or cyclic $C_1$-$C_{12}$ alkyl group, and the substituent thereof is a functional group selected from the group consisting of a maleimido group, amino group, carboxyl group, thiol group, hydroxyl group and active ester group, which may be protected, $R_2$ represents a hydrogen atom, saturated or unsaturated $C_1$-$C_{30}$ aliphatic carbonyl group or arylcarbonyl group, $R_3$ represents —O—$R_5$ or —NH—$R_5$, in which $R_5$, which may be the same or different, represents a hydrophobic group, $R_4$ represents a hydroxyl group, saturated or unsaturated $C_1$-$C_{30}$ aliphatic oxy group or aryl-lower alkyloxy group, L₁ and L₂ independently from each other represent a linker, m represents an integer of 5 to 1000, n represents an integer of 0 to 1000, p represents an integer of 1 to 1000, q represents an integer of 1 to 1000, provided that p accounts for 20% to less than 90%, and preferably 25% to 50%, of the total number of polyamino acid units in the block copolymer, n, p and q are present randomly in the case n is present, p and q are present randomly in the case n is not present, and y represents an integer of 1 or 2).

Although there are no limitations on the linker, since linker can be changed according to the production method of the block copolymer, examples of L₁ include —Z—NH—, —CO—Z—NH— and —CO—NH—Z—NH— (wherein, Z independently represents a $C_1$-$C_8$ alkyl group), and examples of L₂ include —CO—Z—, —Z—CO—, —CO—Z—CO—, —Z—CO—Z— and —Z—CO—O—Z— (wherein, Z independently represents a $C_1$-$C_8$ alkyl group).

The aforementioned block copolymer can be synthesized by, for example, reacting hydrazine or hydrazine hydrate with a known MeO-PEG poly(β-benzyl-L-aspartate) to substitute the benzyl ester moiety thereof with a hydrazide group. This reaction is normally carried out in a dehydrated solvent. An aliphatic or aromatic organic solvent is used for the solvent, and a solvent in which the block copolymer and hydrazine or hydrazine hydrate dissolves therein is preferable. Examples of solvents that are used preferably include N,N-dimethylformamide, N,N-dimethylacetoamide, tetrahydrofuran, dichloromethane, chloroform, N-methyl-2-pyrrolidone and mixed solvents thereof. In addition, the solvent used is preferably as close to being free of water as possible. The amount of hydrazine added during synthesis is normally the amount desired to be added with respect to the benzyl ester moiety of the block copolymer since the reaction proceeds essentially quantitatively. For example, in the case of introducing hydrazine for 50% of the benzyl ester moiety, hydrazine is added at 0.5 times the equivalent of the benzyl ester moiety and in the case of introducing hydrazine for 75% of the benzyl ester moiety, hydrazine is added at 0.75 times the equivalent of the benzyl ester moiety. The reaction is carried out within a range of 0° C. to 100° C., preferably within a range of 20° C. to 80° C., and more preferably within a range of 25° C. to 50° C. The reaction is preferably carried out at normal pressure. Although there are no particular limitations thereon provided the reaction is allowed to proceed adequately, the reaction time is normally 2 hours to 2 days.

In addition, although there are no particular limitations for the amount of epirubicin to be conjugated to the block copolymer as long as retention in the blood is able to be maintained, the amount of epirubicin to be conjugated to the block copolymer is an amount equal to 10% to 50%, preferably 10% to 40%, and in consideration of efficacy and stability, particularly preferably 15% to 35% of the total number of polyamino acid units in the block copolymer. Furthermore, although a plurality of ketones are present in epirubicin, the ketone that covalently bonds with a hydrazide group is preferably the ketone at position 13.

Bonding of epirubicin to the block copolymer is achieved by only reacting epirubicin with the hydrazide groups of the block copolymer preferably under conditions as close to anhydrous conditions as possible. The block copolymer according to the present invention is preferably dissolved in a dehydrated solvent such as N,N-dimethylformamide, dimethylsulfoxide, N,N-dimethylacetoamide, tetrahydrofuran, dichloromethane, chloroform or a mixed solvent thereof, and a desired amount of epirubicin is reacted by adding, for example, 0.1 equivalents to 10 equivalents, and preferably 0.1 equivalents to 3 equivalents, with respect to the number of hydrazide groups. The reaction is carried out over a temperature range of 0° C. to 50° C., preferably over a range of 20° C. to 40° C., and more preferably over a range of 25° C. to 37° C. The reaction is preferably carried out at normal pressure. Although there are no particular limitations for the reaction time as long as the reaction is allowed to proceed adequately, the reaction time is normally 2 hours to 5 days. The solution obtained following the reaction is poured into a suitable hydrophilic organic solvent, for example alcohols, such as 2-propanol, followed by recovering prepicitation by carrying out a washing step. Recovering step may be carried out by a centrifugal separation procedure. The epirubicin-conjugated block copolymer may be further purified by gel filtration or ultrafiltration and the like as necessary to remove unbound drug.

The block copolymer used in the polymeric micelle of the present invention may be only composed of an epirubicin-conjugated block copolymer having epirubicin conjugated with hydrazide groups, or may be composed of (1) a block copolymer composed of a water-soluble polymeric region consisting of polyethylene glycol and a polyamino acid region having a hydrazide group, and optionally a hydrophobic group, in a side chain thereof, wherein the epirubicin is bound to a hydrazide group thereof, and (2) a block copolymer composed of a water-soluble polymeric region consisting of polyethylene glycol and a polyamino acid region and/or derivative thereof having a hydrophobic group, wherein epirubicin is not bound. Examples of block copolymers described in (1) above in a form in which a drug is not bound include those represented by the following formulas:

[Chemical Formula 14]

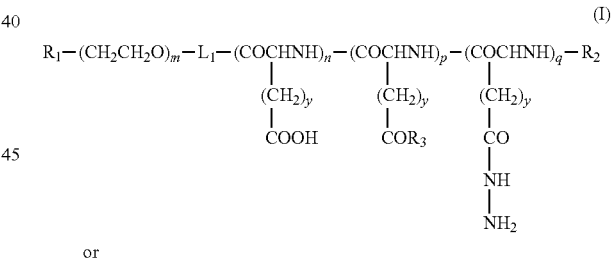

or

[Chemical Formula 15]

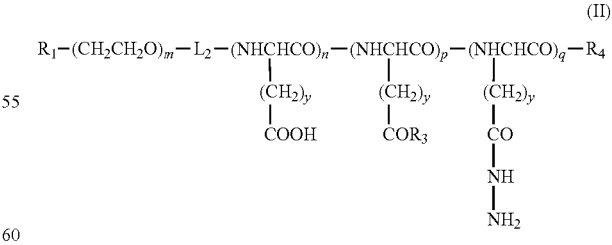

(wherein,

R₁, which may be the same or different, represents a hydrogen atom, methoxy group, methyl group, substituted linear, branched or cyclic $C_1$-$C_{12}$ alkyl group, and the substituent thereof is a functional group selected from the group consisting of a maleimido group, amino group, carboxyl group, thiol group, hydroxyl group and active ester group, which may be protected, $R_2$ represents a hydrogen atom, saturated or unsaturated $C_1$-$C_{30}$ aliphatic carbonyl group or arylcarbonyl group, $R_3$ represents —O—$R_5$ or —NH—$R_5$ in which $R_5$, which may be the same or different, represents a hydrophobic group, $R_4$ represents a hydroxyl group, saturated or unsaturated $C_1$-$C_{30}$ aliphatic oxy group or aryl-lower alkyloxy group, $L_1$ and $L_2$ independently from each other represent a linker, and although there are no particular limitations thereon provided it can be changed according to the production method of the block copolymer, examples of $L_1$ include —Z—NH—, —CO—Z—NH— and —CO—NH—Z—NH— (wherein, Z independently represents a $C_1$-$C_8$ alkyl group), and examples of $L_2$ include —CO—Z—, —Z—CO—, —CO—Z—CO—, —Z—CO—Z— and —Z—CO—O—Z— (wherein, Z independently represents a $C_1$-$C_8$ alkyl group), m represents an integer of 5 to 1000,
n represents an integer of 0 to 1000,
p represents an integer of 1 to 1000,
q represents an integer of 1 to 1000, and
y represents an integer of 1 or 2).

Introduction of hydrazide groups and bonding of epirubicin in the aforementioned block copolymer can be carried out in compliance with the previously explained method for producing an epirubicin-conjugated block copolymer.

In addition, examples of the block copolymer described in above item (2) include those represented by the following formulas:

[Chemical Formula 16]

$$R_1—(CH_2CH_2O)_m—L_1—(COCHNH)_n—(COCHNH)_p—R_2$$
with side chains $(CH_2)_y$—COOH and $(CH_2)_y$—COR_3

[Chemical Formula 17]

$$R_1—(CH_2CH_2O)_m—L_2—(NHCHCO)_n—(NHCHCO)_p—R_4$$
with side chains $(CH_2)_y$—COOH and $(CH_2)_y$—COR_3

(wherein, $R_1$, $R_2$, $R_3$, $R_4$, $L_1$, $L_2$, m, n, p and y are the same as defined in formulas (I) and (II), provided that the amount of p in the sum of n+p accounts for 50% to 100% of the total, and in the case n is present, n and p are present in random or block form).

Although there are no particular limitations on the mixing ratio of the block copolymer in which epirubicin is conjugated in the block copolymer described in (1) above and the block copolymer described in (2) above, the block copolymers of (1) and (2) can be mixed within a range of 1:1 to 9:1. In that case, the ratio of hydrophobic groups to the total number of polyamino acids in the entire block copolymer mixture is 35% to less than 95% and preferably 50% to less than 95%. At this time, hydrophobic groups can be present in either of the copolymers described in (1) and (2) above. The ratio of conjugated epirubicin is 5% to 65%, preferably 5% to 50%, and more preferably 5% to 20% of the total number of polyamino acids in the entire block copolymer mixture.

The epirubicin bound to the block copolymer is an anthracycline-based anti-cancer agent that is used for the treatment of numerous cancers including leukemia, lymphoma, breast cancer, uterine cancer, ovarian cancer, stomach cancer, liver cancer, lung cancer and urothelial carcinoma. The epirubicin can also be in the form of any pharmaceutically acceptable salt.

The anti-cancer agent incorporated in the micelle of the present invention refers to an anti-cancer agent other than epirubicin, and the anti-cancer agent-incorporating epirubicin micelle of the present invention can be clearly distinguished from a micelle in which a portion of the epirubicin has been released from an epirubicin micelle into the micelle. The incorporated anti-cancer agent preferably demonstrates at least one, and more preferably two or more, of actions consisting of ABC transporter inhibitory action, apoptosis-inducing action, cell cycle G2/M checkpoint removal and glucose transporter suppressive action. Thus, the anti-cancer agent of the present invention can also be said to be an ABC transporter inhibitor, apoptosis inducer, cell cycle G2/M checkpoint remover or glucose transporter inhibitor. The anti-cancer agent of the present invention also demonstrates cytotoxicity against cancer stem cells in particular due to the aforementioned actions. Thus, the anti-cancer agent of the present invention can also be said to be an anti-cancer stem cell agent, anti-cancer stem cell suppressor or anti-cancer stem cell inhibitor.

The micelle of the present invention can further incorporate an anti-cancer agent such as an ABC transporter inhibitor inside the hydrophobic core of the micelle formed by the epirubicin-conjugated block copolymer. The incorporated ABC transporter inhibitor can be a compound having an indolocarbazole backbone, a compound having a nitrogen-containing two-member ring, or a compound having a plurality of aromatic rings.

Examples of a compound having an indolocarbazole backbone include compounds represented by the following formula or a salt thereof:

[Chemical Formula 18]

(wherein,

X and Y independently represent H, OH, Cl, a propoxy group or an ethylthiomethyl group, $R_6$ represents H, a $C_{1-3}$ alkyl group, —$NH_2$, benzyl group,

[structure with —N(H)—CH(CH_2OH)(CH_2OH)]

or

[structure with —CH_2CH_2—N(CH_2CH_3)_2], $R_7$ and $R_8$ independently from each other represent H, —OH or a methoxy group, or together with each other form O=, $R_9$ and $R_{10}$ respectively and independently represent a hydrogen atom, methyl group, β-D-glucopyranosyl group, 4-O-methyl-β-D-glucopyranosyl group, cyanoethyl group or

[Chemical Formula 19]

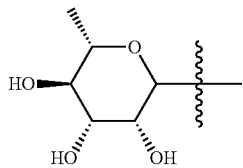

or together with each other form

[Chemical Formula 20]

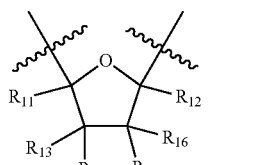

or

[Chemical Formula 21]

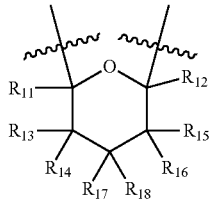

wherein, $R_{11}$ represents a methyl group, $R_{12}$ represents H, $R_{13}$ and $R_{14}$ independently from each other represent H, a methoxy group, —OH, hydroxymethyl group, methylcarboxylate group, methylamino group, methylaminomethyl group, propylaminomethyl group, dimethylamino group or

[Chemical Formula 22]

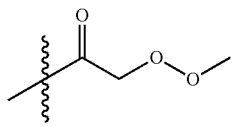

$R_{15}$ and $R_{16}$ independently from each other represent, H, OH or

[Chemical Formula 23]

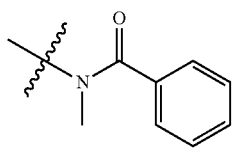

and, $R_{17}$ and $R_{18}$ represent H, OH, a methylamino group, dimethyl amino group, oxime group,

[Chemical Formula 24]

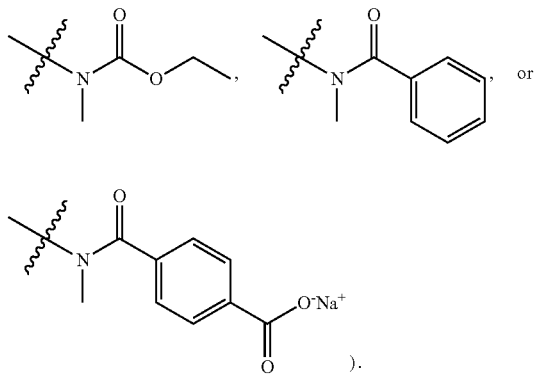

Said indlocarbazlole compound has anti-cancer activity.

Although the indolocarbazole compound used in the present invention may be an arbitrary optical isomer, it is preferably a compound of an optical isomer represented by the following formula:

[Chemical Formula 25]

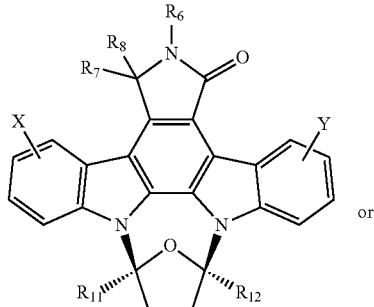

or

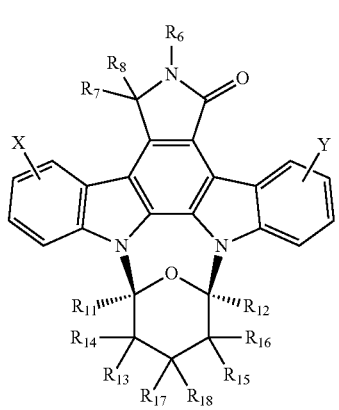

(wherein,

X, Y, $R_6$ to $R_8$ and $R_{11}$ to $R_{18}$ are as previously defined above).

From the viewpoint of filling into the micelle of the present invention, the indolocarbazole compound used in the present invention is preferably a compound represented by the following formula:

[Chemical Formula 26]

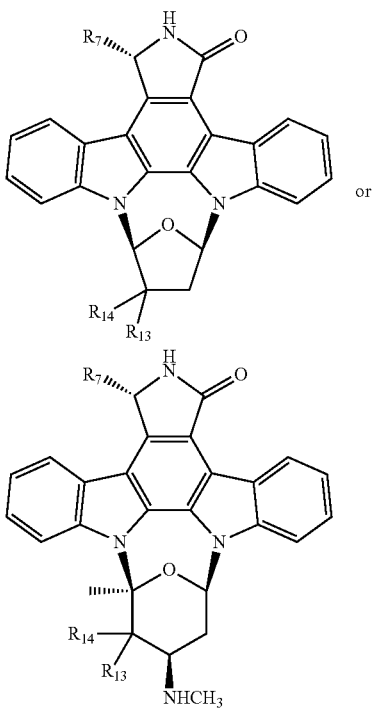

or (wherein,

R$_7$ represents H or OH, and

R$_{13}$ and R$_{14}$ respectively and independently represent H, a methoxy group, —OH or a hydroxymethyl group).

Examples of compounds having an indolocarbazole backbone used in the present invention include the following compounds: staurosporine, 7-hydroxystaurosporine, KT5926, staurosporine aglycone, SF2370, KT5823, 4'-N-benzoylstaurosporine, PKC412, Go6976, N,N-dimethylstaurosporine, NA 0359, N-ethoxycarbonyl-7-oxostaurosporine, KT-6124, CGP42700, 4'-demethylamino-4',5'-dihydroxystaurosporine, 7-oxostaurosporine, CEP751, NA0346, NA0359, 3'-demethoxy-3'-hydroxystaurosporine, KT 6006, 7-O-methyl-UCN 01, TAN 999, NA 0346, NA 0345, NA 0344, CGP44171A, SCH47112, N,N-dimethylstaurosporine, TAN1030A, lestaurtinib, 4'-demethylamino-4'-hydroxystaurosporine, AFN941, edotecarin and salts thereof.

Examples of ABC transporter inhibitors in the form of compounds having a nitrogen-containing two-member ring used in the present invention include compounds having an indazole backbone such as axitinib or pazopanib, compounds having a quinazoline backbone such as vandetanib, aftatinib, bosutinib, canertibin, cediranib, erlotinib, gefitinib or lapatinib, and other compounds having a nitrogen-containing two-member ring such as ponatinib, vemurafenib, tofacitinib, sunitinib or danusertib, and pharmaceutically acceptable salts thereof.

Examples of ABC transporter inhibitors in the form of compounds having one or a plurality of aromatic rings used in the present invention include dabrafenib, imatinib and nilotinib having four aromatic rings, crizotinib, dasatinib, regorafenib and sorafenib having three aromatic rings, and tandutinib having a single aromatic ring, and pharmaceutically acceptable salts thereof.

In the present invention, a pharmaceutically acceptable salt refers to any arbitrary salt provided it does not impair the activity of the compound, examples of which include hydrochlorides, nitrates, hydrobromates, phosphates, bisulfates, alkyl sulfonates, aryl sulfonates, acetates, benzoates, citrates, maleates, fumarates, succinates, lactates and tartrates.

The ABC transporter inhibitor used in the present invention is able to act by inhibiting the drug elimination mechanism of cancer cells and more preferably drug-resistant cancer cells such as cancer stem cells. Thus, the concomitant use thereof with epirubicin makes it possible to radically cure cancer while reducing the possibility of recurrence. Thus, the ABC transporter inhibitor in the present invention can also be referred to as an anti-cancer agent. Without intending to be limited by theory, the ABC transporter inhibitor of the present invention is able to bind to protein ATP binding sites enabling it to effectively suppress kinase and transporter activity.

An indolocarbazole compound, which is one of ABC transporter inhibitor used in the present invention, is thought to be able to exert a considerably high antitumor effect and/or anti-cancer activity, by demonstratingat least one, and more preferably two or more, of actions consisting of apoptosis-inducing action, cell cycle G2/M check point removal, suppression of ABC transporters contributing to cancer cell resistance, and glucose transporter suppressive action. Among these, inhibition of protein kinase C in particular has been shown through research conducted by the inventors of the present invention to be particularly effective against cancer stem cells, and indolocarbazole compounds that inhibit protein kinase C are thought to be extremely useful in the treatment or radical cure of tumors and cancers containing cancer stem cells. On the other hand, as a result of binding to and acting on a wide range of proteins having ATP binding sites in this manner, indolocarbazole compounds often have potent adverse side effects, and due to their high level of hydrophobicity, have frequently been difficult to develop into pharmaceuticals. According to the present invention, problems involving the adverse side effects and/or hydrophobicity of indolocarbazole compounds were able to be solved by incorporating an indolocarbazole compound in a micelle formed with an epirubicin-conjugated copolymer, thereby enabling the development of a DDS pharmaceutical that has few adverse side effects and is highly effective against tumors. In the micelle of the present invention, although the indolocarbazole compound is thought to be present in the hydrophobic region within the core of the micelle, a portion thereof may not be present in the core depending on the production method used.

An epirubicin-conjugated copolymer and an anti-cancer agent are incorporated in the micelle of the present invention at an arbitrary weight ratio, and are preferably present within a range of, for example, 5:2 to 10:1. From the viewpoint of ensuring suitable dispersibility, the size of the micelle is such that the weight ratio of the anti-cancer agent to the epirubicin-conjugated copolymer is preferably 1 or less, more preferably 0.8 or less and even more preferably 0.5 or less. From the viewpoint of enhancing the filled amount of the anti-cancer agent, the weight ratio of the anti-cancer agent to the epirubicin-conjugated copolymer is preferably 0.1 or more, more preferably 0.2 or more and even more preferably 0.4 or more. The epirubicin-conjugated copolymer and anti-cancer agent demonstrate a synergistic effect that exceeds their additive effect in terms of their antitumor effect.

The micelle of the present invention can be acquired by mixing an epirubicin-conjugated block copolymer and a solution of an anti-cancer agent and evaporating the solvent from the mixed solution followed by adding a different solvent, dissolving the aforementioned components therein and carrying out sonication to incorporate the anti-cancer agent within the inner core of a micelle formed by the epirubicin-conjugated block copolymer. Any arbitrary solvent can be used provided it is able to dissolve the anti-cancer agent and epirubicin-conjugated block copolymer, and an organic solvent such as alcohols can be used in order to dissolve a hydrophobic anti-cancer agent, for example. The solvent used during sonication may be any arbitrary solvent provided it is able to stably maintain the micelle formed, water is used preferably from the viewpoint of administering the resulting micelle into the body, while a buffered aqueous solution can be used from the viewpoint of protecting the micelle. A micelle having a desired size can be selected by passing the resulting micelle once or a plurality of times through a prescribed filter.

In another embodiment, the present invention relates to a pharmaceutical composition for the treatment of cancer that contains a micelle containing an anti-cancer agent and an epirubicin-conjugated block copolymer. Examples of diseases able to be treated with this therapeutic composition include any cancer or tumor such as neuroblastoma, liver cancer, malignant melanoma, uterine cancer, bladder cancer, bile duct cancer, esophageal cancer, osteosarcoma, testicular tumor, thyroid cancer, acute myelogenous leukemia, brain tumor, prostate cancer, pancreatic cancer, head and neck squamous cell carcinoma, mesothelioma, lung cancer, colon cancer, kidney cancer, ovarian cancer and breast cancer. Since the therapeutic composition of the present invention is able to act on cancer stem cells, it is useful in the treatment of cancers or tumors containing cancer stem cells. Known examples of cancers or tumors containing cancer stem cells include, but are not limited to, acute myelogenous leukemia, brain tumor, prostate cancer, pancreatic cancer, head and neck squamous cell carcinoma, mesothelioma, lung cancer, colon cancer, kidney cancer, ovarian cancer and breast cancer. Since the micelle of the present invention contains epirubicin, it can be used to treat any cancer provided epirubicin is indicated for the treatment thereof, and is able to demonstrate therapeutic efficacy against cancer that has acquired resistance to epirubicin as a result of treatment with epirubicin or an epirubicin micelle. Among these cancers, a micelle containing an anti-cancer agent and epirubicin-conjugated block copolymer is extremely useful in terms of being able to treat kidney cancer and ovarian cancer, which are known to be difficult to treat.

In still another aspect, the present invention relates to a method for treating, preventing or mitigating a disease such as neuroblastoma, liver cancer, malignant melanoma, uterine cancer, bladder cancer, bile duct cancer, esophageal cancer, osteosarcoma, testicular tumor, thyroid cancer, acute myelogenous leukemia, brain tumor, prostate cancer, pancreatic cancer, head and neck squamous cell carcinoma, mesothelioma, lung cancer, colon cancer, kidney cancer, ovarian cancer or breast cancer comprising administration of an effective amount of the micelle or pharmaceutical composition of the present invention to a patient requiring treatment, prevention or mitigation of these diseases. Since the micelle or pharmaceutical composition of the present invention is able to act on cancer stem cells, it is useful for the treatment or prevention of cancers or tumors containing cancer stem cells. Examples of cancers or tumors containing cancer stem cells include, but are not limited to, acute myelogenous leukemia, brain tumor, prostate cancer, pancreatic cancer, head and neck squamous cell carcinoma, mesothelioma, lung cancer, colon cancer, kidney cancer, ovarian cancer and breast cancer. The preventive method may be any of a method for preventing cancer proliferation, metastasis or recurrence.

The micelle or pharmaceutical composition of the present invention is useful for the treatment of cancer or tumors having drug resistance. Drug resistance may be resistance to any anti-cancer agent. Some cancer cells may acquire resistance by eliminating the drug through an ATP-binding cassette transporter (ABC transporter). ABC transporters are able to not only eliminate drugs that are currently being administered, but also eliminate other drugs as well, and are therefore thought to contribute to multidrug resistance. Examples of drug resistance include, but are not limited to, drug resistance to anti-cancer agents such as epirubicin, cisplatin, etoposide, vincristine, taxol, camptothecin or mitoxantrone, and the micelle or pharmaceutical composition of the present invention can be used for the treatment, mitigation or prevention of cancers or tumors having resistance to these anti-cancer agents. Although the reason for the micelle or pharmaceutical composition of the present invention being effective against drug-resistance cancers or tumors is thought to be based on indolocarbazole compounds, including staurosporine, having ABC transport inhibitory activity, it is not limited thereto. Without intending to be limited by theory, indolocarbazole compounds, including staurosporine, are thought to inhibit activity by binding to the ATP pocket of an ABC transporter (NPLs 12, 13 and 14). Examples of ABC transporters inhibited by indolocarbazole compounds include MDRs (MDR1, MDR2 and MDR3), MRPs (MRP1 to MRP9), BCRP, ABCA and BSEP.

A preparation containing the micelle of the present invention may be provided in the form of a solution or may be provided in the form of a powder that is reconstituted with water, buffer or physiological saline and the like prior to use. In the case of reconstituting prior to use, a desired micelle size can be selected by carrying out sonication or filtration treatment. Although a preparation in the form of a solution or a reconstituted preparation can be administered by any arbitrary route, examples thereof include parenteral administration, such as intravenous, intraperitoneal, intraarterial, intramuscular, subcutaneous, intrapleural, intrathecal and intrarectal administration. The administration schedule of a preparation containing the micelle can be suitably selected by a physician corresponding to the status of the tumor or cancer. Desired effects can be demonstrated by administering according to an administration schedule consisting of, for example, once every few days, once a week, once every ten days or once every two days. On the other hand, administration can also be performed once to several times per day, such as by administering once a day, twice a day or three times a day. The dosage per administration can be selected arbitrarily corresponding to the administration schedule, and in the case of administering in the form of a micelle, for example, the dosage can be 0.1 mg/kg to 100 mg/kg (body weight). From the viewpoint of reducing toxicity, the dosage is preferably 50 mg/kg or less and more preferably 20 mg/kg or less, while from the viewpoint of efficacy, the dosage is preferably 0.5 mg/kg or more and more preferably 1.0 mg/kg or more.

A preparation containing the micelle of the present invention may further contain an additional active ingredient other than or in addition to an anti-cancer agent. Although a compound approved for use as an anti-cancer agent is preferable for such an active ingredient, an unapproved compound may also be used. Examples of compounds incorporated in epirubicin micelles include reserpine, etoposide and camptothecin. These additional active ingredients may be arranged within the core of the micelle in the same manner as the epirubicin and anti-cancer agent, or may simply be mixed with an anti-cancer agent-containing epirubicin micelle. In addition to these active ingredients, a preparation containing the micelle of the present invention can also use an arbitrary excipient able to be used in pharmaceutical preparations provided it does not impair the stability of the micelle, and examples thereof which can be used include pH buffers, preservatives and emulsifiers.

EXAMPLES

Example 1

Method for Preparing Epirubicin Micelle Incorporating Indolocarbazole Compound A solution obtained by dissolving a powder of PEG-b-(PBLA-hydrazide-epirubicin) copolymer (PEG weight average molecular weight (Mw)=12,000 Da, No. of PBLA units=40, No. of epirubicin units=8, NanoCarrier Co., Ltd., Japan) (equivalent to 20 mg of epirubicin) in 40 ml of methanol and a solution obtained by dissolving 4 mg of staurosporine (Funakoshi Co., Ltd., Japan) in 10 ml of methanol were mixed in a pear-shaped flask for 30 minutes at room temperature with a stirrer. The mixed solution was applied to a rotary evaporator (N-1200AV (Elyra)) followed by evaporating the methanol. After having evaporated the methanol, HEPES buffer (10 mM, pH 7.4, 50 ml) was added to the flask followed by carrying out sonication for 30 minutes (Bioruptor, Cosmo Bio Co., Ltd., Japan). Subsequently, the solution was passed through a polyethersulfone (PES) filter (0.22 μm) (Millipore Corp.). The solution was further purified by subjecting to five rounds of ultrafiltration (molecular weight cutoff: 30,000 Da) (Centricon Plus-20, Millipore Corp.) for 15 minutes (while adding 5 ml of HEPES buffer (10 mM, pH 7.4) for each round of ultrafiltration) followed by concentrating to 15 ml. Finally, the solution was passed through a PES filter (0.22 μm).

The particle size of the resulting micelle was measured by DLS (Zetasizer (Malvern Instruments Ltd.). The concentrations of epirubicin and staurosporine in the micelle were measured using a calibration curve determined by HPLC (LC-2000, Jasco Corp.) using a TSK-Gel (TSK Corp.) column to quantify the contents thereof.

Micelles were also produced using the same method as described above using UCN-01 (Sigma), PKC412 (Wako), reserpine (Sigma), CEP701/lestaurtinib (Merck), vismodegib (Iwai Chemicals) and enzastaurin (Iwai Chemicals) instead of staurosporine. Staurosporine, UCN-01, PKC412, reserpine and CEP701/lestaurtinib were able to be detected in the micelles (FIGS. 1B to 1F). On the other hand, vismodegib and enzastaurin were unable to be detected in the micelles (data not shown).

Next, the same experiment was carried out while changing only the weights of the staurosporine and PEG-b-(PBLA-hydrazide-epirubicin) copolymer. Staurosporine was incorporated in epirubicin micelles using 1 mg, 2.5 mg or 5 mg of staurosporine to an amount of PEG-b-(PBLA-hydrazide-epirubicin) copolymer equivalent to 5 mg, 2.5 mg or 2.5 mg of epirubicin. The concentrations of epirubicin and staurosporine in the micelles in which they were incorporated were measured by HPLC (LC-2000, Jasco Corp.) using a TSK-Gel (TSK Corp.) column (FIG. 1G). Although complete incorporation of staurosporine in the micelle was observed in the case of an epirubicin:staurosporine weight ratio of 5:1, dispersibility increased at a weight ratio of 1:1 and polydispersivity increased at a ratio of 1:2, which was unsuitable for used as an incorporating micelle.

Example 2

Measurement of Release Characteristics of Staurosporine-Incorporating Epirubicin Micelle The pH-sensitive release characteristics of epirubicin and staurosporine were investigated in a micelle formed using amide bonds instead of pH-sensitive hydrazide bonds for the bonds between the epirubicin and block copolymer in the epirubicin-conjugated block copolymer used in the micelle of the present invention. 0.3 ml aliquots of micelle suspensions (1 mg/ml Epi, 0.2 mg/ml STS) were placed in dialysis bags (Slide-A-Lyzer Dialysis Cassettes, 3.5 K MWCO, Thermo Fisher Scientific K.K.). The dialysis bags were placed in HEPES buffer (30 ml) having different pH (pH 5.5, pH 6.5 or pH 7.4) followed by stirring the micelle suspensions with a stirrer at room temperature. 0.5 ml samples of the outside buffer were collected after the passage of 1 hour, 4 hours, 20 hours, 48 hours, 72 hours, 96 hours and 120 hours followed by measurement of the concentrations of epirubicin and staurosporine by HPLC (FIGS. 2A and 2B).

Measurement of In Vitro Anti-Cancer Activity

Anti-cancer activity was measured according to the method indicated below using the Cell Counting Kit-8 (Dojindo, Japan). Mesothelioma cell line MSTO-211H cells were disseminated at $1 \times 10^3$ cells/well to $3 \times 10^3$ cells/well. The medium was replaced on the following day followed by the addition of 50 μl of medium. Moreover, dilution series of epirubicin micelle (Epi micelle), pH-sensitive staurosporine-incorporating epirubicin micelle (STS Epi Micelle pH) and pH non-sensitive staurosporine-incorporating epirubicin micelle (STS Epi Micelle amide) were prepared and added at 50 μl/well followed by stirring. 72 hours later, 10 μl of Cell Counting Kit-8 were added followed by measuring optical absorbance at 450 nm 1 hour later with a microplate reader (Model 680, BioRad, Hercules, Calif.). Cell survival rates were calculated according to the equation indicated below based on the measured optical absorbance and are shown in the graph (FIG. 2C). These were plotted on the graph for each drug and the value corresponding to a survival rate of 50% was taken to be the $IC_{50}$ value (concentration of drug resulting in 50% cytotoxicity).

Cell survival rate (%)=[(As−Ab)/(Ac−Ab)]×100    [Equation 1]

In the equation, As indicates the optical absorbance of the specimen (wells containing cells, test substance and Cell Counting Kit solution), Ac indicates the optical absorbance of a negative control (wells containing only cells and Cell Counting Kit solution) (absence of test substance), and Ab indicates the optical absorbance of a blank (cell-free wells containing only medium and Cell Counting Kit solution).

Tumor Growth Test (Drug Sensitivity Test) A subcutaneous implantation model was prepared for use in evaluating efficacy by subcutaneously implanting MSTO-211H mesothelioma cells in female nude mice. MSTO-211H mesothelioma cells were cultured, and 100 μl of cells having a concentration of $4 \times 10^7$ cells/ml were mixed with an equal volume of Matrigel (Becton Dickinson, 100 μl) followed by implanting 200 μl of the mixture ($2 \times 10^6$ cells/animal) beneath the skin. Five days after implant, the day on which tumor diameter was confirmed to have reached 4 mm to 5 mm was designated as Day 0. Epirubicin micelle (Epi micelle), pH-sensitive staurosporine-incorporating epirubicin micelle (STS Epi Micelle pH) and pH non-sensitive staurosporine-incorporating epirubicin micelle (STS Epi Micelle amide) were administered four times into the caudal vein of the tumor-laden mice at a dosage of 4 mg/kg on day on Days 0, 4, 8 and 12. The major axis (a) and minor axis (b) of the tumor were measured with a caliper twice a week to determine tumor volume ($mm^3$) using the formula $(ab)^2/2$ (FIG. 2D).

Example 3

Synergistic Effect of Staurosporine and Epirubicin and Verification of Effect of Micelle Incorporation During Addition of Blood Protein hAGP Verification of Effect of Micelle Incorporation During Addition of hAGP Anti-cancer activity was measured according to the method indicated below using the Cell Counting Kit-8 (Dojindo, Japan). Mesothelioma cell line MSTO-211H cells were disseminated at $1\times10^3$ cells/well to $3\times10^3$ cells/well and cultured. The medium was replaced on the following day followed by the addition of 50 μl of medium. Epirubicin was added at 125 ng/ml followed by the addition of staurosporine while changing the concentration thereof to 0 ng/ml, 25 ng/ml, 62.5 ng/ml or 125 ng/ml. A group to which anti-cancer agent was not added (No Treat) and a group to which only staurosporine was added (STS 125 ng/ml) were used as controls. 72 hours later, 10 μl of Cell Counting Kit-8 were added followed by measuring optical absorbance at 450 nm 1 hour later with a microplate reader (Model 680, BioRad, Hercules, Calif.). Cell survival rates (%) were calculated by applying the measured optical absorbance values to the following equation (FIG. 3A).

$$\text{Cell survival rate (\%)} = [(As-Ab)/(Ac-Ab)] \times 100 \quad \text{[Equation 2]}$$

In the equation, As indicates the optical absorbance of the specimen (wells containing cells, test substance and Cell Counting Kit solution), Ac indicates the optical absorbance of a negative control (wells containing only cells and Cell Counting Kit solution) (absence of test substance), and Ab indicates the optical absorbance of a blank (cell-free wells containing only medium and Cell Counting Kit solution).

The mixture of staurosporine and epirubicin was able to decrease survival rate dependent on the concentration of staurosporine, and demonstrated a synergistic effect in comparison with administration of epirubicin alone or staurosporine alone.

The test substances were divided into groups obtained by adding epirubicin micelle (Epi micelle) (containing 0.1 μg/ml of epirubicin), staurosporine-incorporating epirubicin micelle (STS Epi micelle) (containing 0.02 μg/ml of STS and 0.1 μg/ml of epirubicin), epirubicin (Epi) (0.1 μg/ml), staurosporine (STS) (0.02 μg/ml) or a mixture of staurosporine at 0.02 μg/ml and epirubicin at 0.1 μg/ml (STS Epi Mix) to 100 μl of the cell preparations prepared above, followed by investigating the effects of the addition of human α-acid glycoprotein at 0.5 mg/ml (FIG. 3B). On the basis of these results, the effects of the staurosporine-incorporating epirubicin micelle and the effects of the mixture of staurosporine and epirubicin were determined to be equal. In addition, since administration of staurosporine alone resulted in a significant increase in cell survival rate in the case of adding hAGP, staurosporine was determined to lose activity as a result of binding with the blood protein, hAGP, indicating that it would be difficult to use in vivo. Incorporation of staurosporine in the epirubicin micelle was not affected by addition of hAGP, thereby demonstrating that deactivation in the blood can be prevented.

Example 4

Induction of Apoptosis by Staurosporine-Incorporating Epirubicin Micelle in Drug-Resistant Strains Mesothelioma (MSTO-211H) cells, lung cancer (H460) cells and breast cancer (MCF-7) cells were cultured in drugs consisting of 0.2 μg/ml epirubicin (NanoCarrier Co., Ltd.), 0.5 μg/ml cisplatin (Cisplatin for Injection, Yakult Honsha Co., Ltd.), and 0.02 μg/ml pematrexed (Alimta for Injection, Eli Lilly Japan K.K.) for 3 months at their prescribed concentrations to establish strains resistant to each drug. The presence or absence of resistance was able to be determined by comparing the resistant strain with the original strain using the aforementioned Cell Counting Kit-8, and the strains were used after confirming to be resistant.

Figure 4:
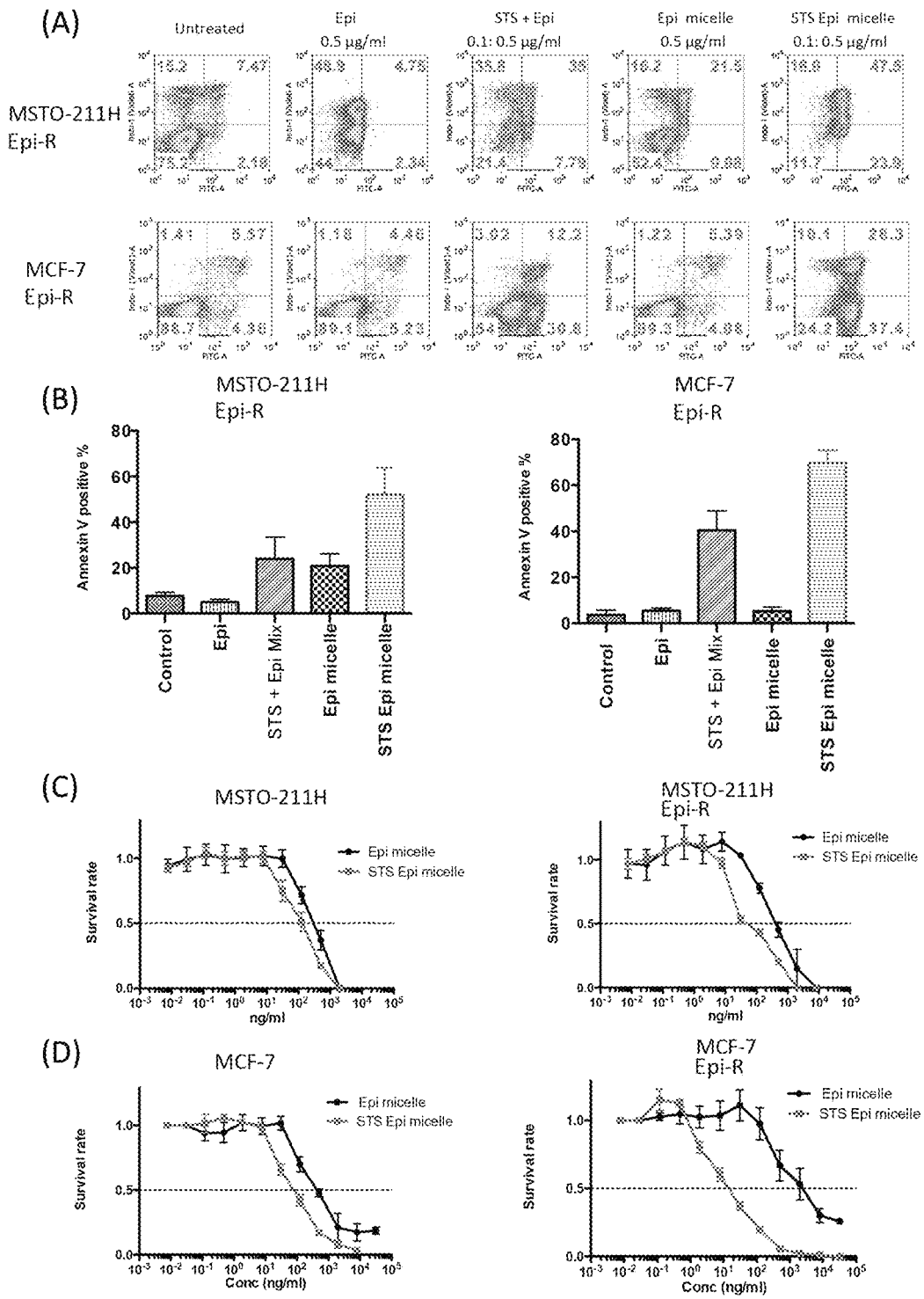
FIG. 4 indicates the apoptosis-inducing effects of epirubicin (Epi), mixture of staurosporine and epirubicin (STS+Epi Mix), epirubicin micelle (Epi micelle) and staurosporine-incorporating epirubicin micelle (STS Epi micelle) on an epirubicin-resistant strain.

Next, epirubicin (Epi), a mixture of staurosporine and epirubicin (STS Epi Mix), epirubicin micelle (Epi micelle) and staurosporine-incorporating epirubicin micelle (STS Epi Micelle) were added to resistant strains of the human mesothelioma cells (MSTO-211H) and breast cancer cells (MCF-7) prepared to a concentration of $1\times10^6$ cells/ml. The cells were then isolated with Accutase and washed with PBS followed by adding 2 μl of Annexin V-FITC and 1 μg/ml of DAPI to 1 ml of the cell suspensions and culturing for 15 minutes in a cool, dark location. After adding 400 μl of incubation buffer, stirring and passing through a mesh, the cell suspensions were analyzed using FACS (BD LSRII, Becton Dickinson) (FIGS. 4A and 4B). Next, epirubicin micelle and staurosporine-incorporating epirubicin micelle were added to the human mesothelioma cells (MSTO-211H) and the resistant strain thereof as well as to the breast cancer cells (MCF-7) and the resistant strain thereof while changing the concentrations thereof followed by investigating cell survival rates using the same procedure as that of Example 3 (FIGS. 4C and 4D).

Example 5

Measurement of In Vivo Anti-Cancer Activity in Subcutaneous Mesothelioma Model

A subcutaneous implantation model was prepared for use in evaluating efficacy by subcutaneously implanting human mesothelioma cells (strain MSTO-211H) in female nude mice. The MSTO-211H cells were cultured, and 100 μl of cells having a concentration of $4\times10^7$ cells/ml were mixed with an equal volume of Matrigel (Becton Dickinson, 100 μl) followed by implanting 200 μl of the mixture ($2\times10^6$ cells/animal) beneath the skin. Five days after implant, the day on which tumor diameter was confirmed to have reached 4 mm to 5 mm was designated as Day 0. Various drugs were administered four times into the caudal vein of the tumor-laden mice in accordance with the following table on Days 0, 4, 8 and 12.

TABLE 1

| Drug | Abbreviation | Staurosporine Equivalent | Epirubicin Equivalent |
|---|---|---|---|
| Epirubicin micelle | Epi Micelle | — | 4 mg/kg |
| Staurosporine-incorporating epirubicin micelle prepared in Example 1 | STS + Epi micelle | 0.8 mg/kg | 4 mg/kg |
| Epirubicin | Epi | — | 4 mg/kg |
| Staurosporine | STS | 0.8 mg/kg | 4 mg/kg |
| Staurosporine and epirubicin mixture | STS Epi Mix | 0.8 mg/kg | 4 mg/kg |
| Staurosporine and epirubicin micelle mixture | Epi Micelle STS Mix | 0.8 mg/kg | 4 mg/kg |

Figure 5:
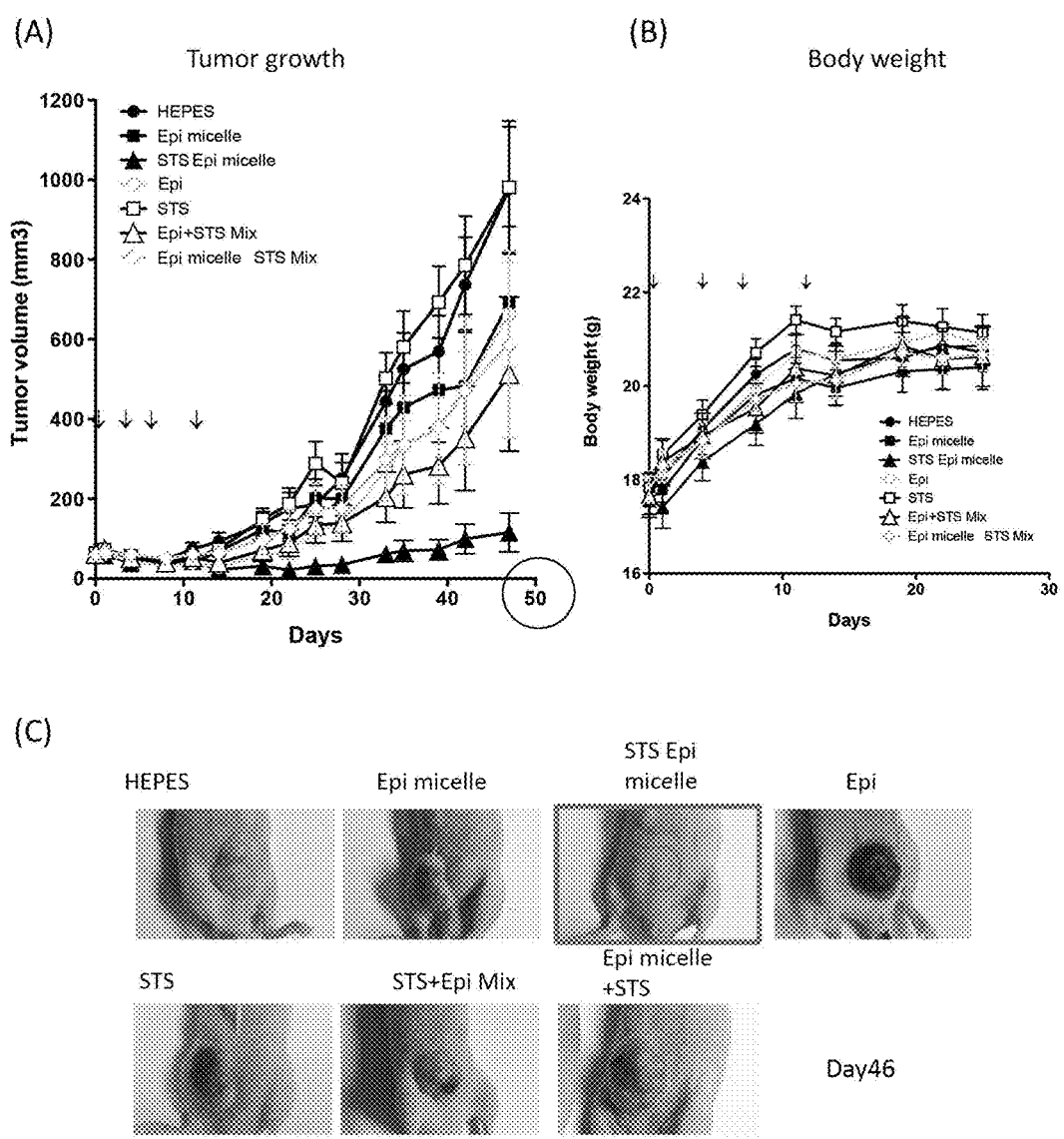
FIG. 5 indicates changes in tumor volume in the case of having intravenously administered an epirubicin micelle (Epi micelle), staurosporine-incorporating epirubicin micelle (STS Epi micelle), epirubicin (Epi), staurosporine (STS) and a mixture of staurosporine and epirubicin (Epi micelle STS Mix) in a subcutaneous solid tumor model of malignant mesothelioma (FIG. 5A), while FIG. 5B indicates changes in body weight during the experimental period, and FIG. 5C indicates the appearance of the tumor on Day 46.

HEPES solution was administered instead of a drug for use as a negative control. The major axis (a) and minor axis (b) of the tumors were measured with a caliper twice a week to calculate tumor volume (mm$^3$) using the formula (ab)$^2$/2 while simultaneously measuring the body weights of the mice (FIGS. 5A and 5B). The tumors were photographed on Day 46 (FIG. 5C).

Example 6

Measurement of In Vivo Anti-Cancer Activity in Orthotopic Mesothelioma Model

Human mesothelioma MSTO-211H was transfected with luciferase based on the method described in Mol. Ther., 2012 April, 20(4), 769-777 to obtain a luciferase-expressing strain (MSTO-211H-luc). MSTO-211H-luc cells were cultured for 3 months in medium containing 0.2 µg/ml of epirubicin to produce epirubicin-resistant human mesothelioma cells (MSTO-211H-luc). 1×10$^6$ of the epirubicin-resistant MSTO-211H-luc cells were administered into the thoracic cavity of female nude mice to produce an orthotopic implant model. Five days after administration, drugs at the dosages shown in the following table were diluted with physiological saline for injection (Otsuka Pharmaceutical Co., Ltd.) and administered into the caudal vein (on Days 5, 9, 13, 23, 33, 43, 53 and 63).

TABLE 2

| Drug | Abbreviation | Staurosporine Equivalent | Epirubicin Equivalent |
|---|---|---|---|
| Epirubicin micelle | Epi Micelle | — | 6 mg/kg |
| Staurosporine-incorporating epirubicin micelle prepared in Example 1 | STS + Epi micelle | 1.2 mg/kg | 6 mg/kg |
| Epirubicin | Epi | — | 6 mg/kg |
| Staurosporine | STS | 1.2 mg/kg | — |
| Staurosporine and epirubicin mixture | STS Epi Mix | 1.2 mg/kg | 6 mg/kg |
| Staurosporine and epirubicin micelle mixture | Epi Micelle STS Mix | 1.2 mg/kg | 6 mg/kg |

Figure 6D:
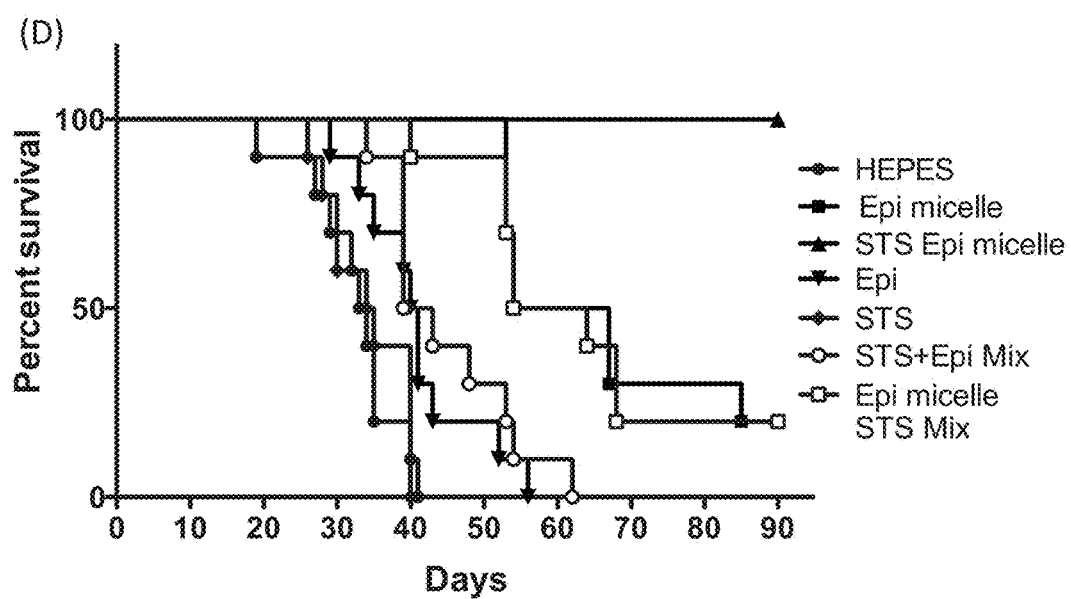
FIG. 6D indicates a graph showing survival rates following administration of various drugs.

HEPES solution was administered instead of a drug for use as a negative control. Staurosporine was injected into the caudal vein after dissolving in DMSO at 5 mg/ml and diluting with physiological saline for injection (Otsuka Pharmaceutical Co., Ltd.). D-luciferin (Summit Pharmaceuticals International Corp.) was administered intraperitoneally, and body weights of the mice were measured simultaneous to measuring luminescence intensity of the luciferase twice a week using an IVIS Imaging System (Summit Pharmaceuticals International Corp.) (FIGS. 6A to 6C). Survival curves were verified according to the Kaplan-Meier method using Prism software (FIG. 6D). Significant differences as determined with a log-rank test were observed between the negative control and Epi (P=0.016), between Epi and Epi Micelle (P=0.0001) and between Epi Micelle and STS+Epi Micelle (P=0.0012).

Example 7

Measurement of In Vivo Anti-Cancer Activity in Subcutaneous Colon Cancer Model

Figure 7:
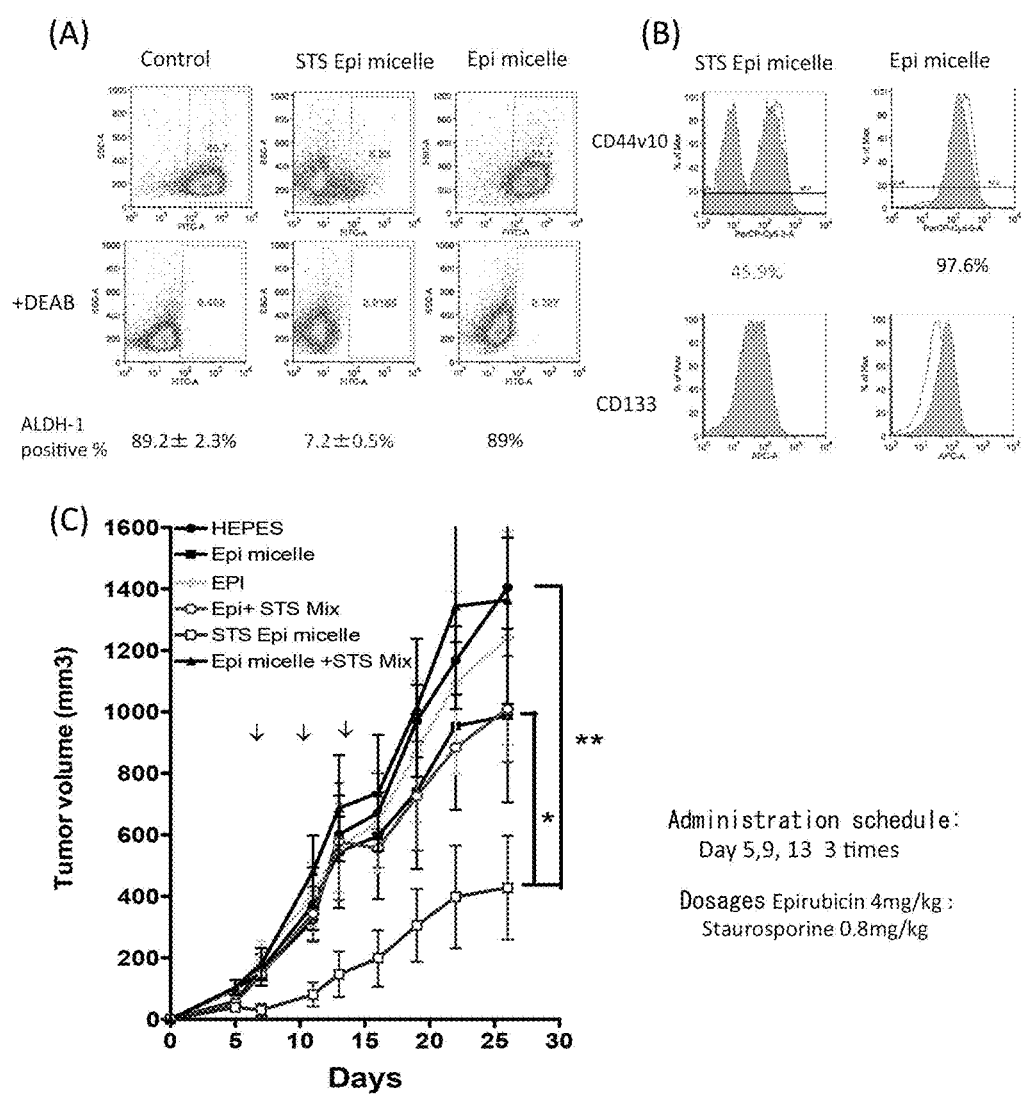
FIG. 7 indicates that a staurosporine-incorporating epirubicin micelle is able to reduce aggregation of cancer stem cells (ALDH-1-positive) in colon cancer (FIG. 7A).

Epirubicin micelle (Epi micelle) and staurosporine-incorporating epirubicin micelle (STS Epi Micelle) were added at 3 µg/ml to a resistant strain of human colon cancer (HT29) prepared to a concentration of 1×10$^6$ cells/ml followed by incubating for 24 hours. 5 µM diethylaminobenzaldehyde (DEAB) was added as a negative control. The incubated cells were then analyzed by FACS (BD LSR II, Becton Dickinson) using an Aldefluor Assay (StemCell Technologies, Durham, N.C., USA) (FIG. 7A).

A subcutaneous implantation model was prepared for use in evaluating efficacy by subcutaneously implanting human colon cancer HT29 cells in female nude mice. The HT29 cells were cultured and 1×10$^6$ cells were implanted beneath the skin of the mice. After 20 to 30 days had elapsed, tumors that had reached a size of 10 mm to 20 mm were sectioned into cubes measuring 2 mm to 3 mm. The uniformly sized sections were implanted beneath the skin of female nude mice. Day 5 after implant (when tumor size reached 4 mm to 5 mm) was designated as Day 0, and the drugs shown in the following table were administered at the prescribed dosages on Days 0, 4 and 8.

TABLE 3

| Drug | Abbreviation | Staurosporine Equivalent | Epirubicin Equivalent |
|---|---|---|---|
| Epirubicin micelle | EPI Micelle | — | 4 mg/kg |
| Epirubicin | Epi | — | 4 mg/kg |
| Staurosporine and epirubicin mixture | STS Epi Mix | 0.8 mg/kg | 4 mg/kg |
| Staurosporine-incorporating epirubicin micelle prepared in Example 1 | STS + Epi micelle | 0.8 mg/kg | 4 mg/kg |
| Staurosporine and epirubicin micelle mixture | Epi Micelle STS Mix | 0.8 mg/kg | 4 mg/kg |

HEPES solution was administered instead of a drug for use as a negative control. The major axis (a) and minor axis (b) of the tumors were measured with a caliper twice a week to calculate tumor volume (mm$^3$) using the formula (ab)$^2$/2 while simultaneously measuring the body weights of the mice (FIGS. 7A and 7B).

Example 8

Measurement of In Vivo Anti-Cancer Activity in Orthotopic Lung Cancer Model

Drug efficacy was evaluated using an orthotopic implant model produced by directly administering cisplatin-resistant human lung cancer H460-luc cells into the lungs of female nude mice to verify the effect of staurosporine micelle on human lung cancer. Luciferase-expressing lung cancer H460-luc cells (JCRB) were cultured for 3 months in medium containing 1 µg/ml of cisplatin to acquire a cisplatin-resistant strain. 2×10$^6$ cells of the cisplatin-resistant strain H460-luc (containing 10% Matrigel (Becton Dickinson) were implanted into the left lower lobe of the lungs of female nude mice in accordance with the method described in Fushiki, et al., Cancer Sci., 2009 August, 100(8). Four days after implant, the drugs indicated in the following table were diluted to their prescribed dosages with physiological saline for injection (Otsuka Pharmaceutical Co., Ltd.) and administered into the caudal vein (on Days 4, 11, 18, 25 and 32).

TABLE 4

| Drug | Abbreviation | Staurosporine Equivalent | Epirubicin Equivalent |
| --- | --- | --- | --- |
| Epirubicin | Epi | — | 6 mg/kg |
| Staurosporine | STS | 1.2 mg/kg | — |
| Staurosporine and epirubicin mixture | STS Epi Mix | 1.2 mg/kg | 6 mg/kg |
| Epirubicin micelle | EPI Micelle | — | 6 mg/kg |
| Staurosporine-incorporating epirubicin micelle prepared in Example 1 | STS + Epi Micelle | 1.2 mg/kg | 6 mg/kg |

Figure 8:
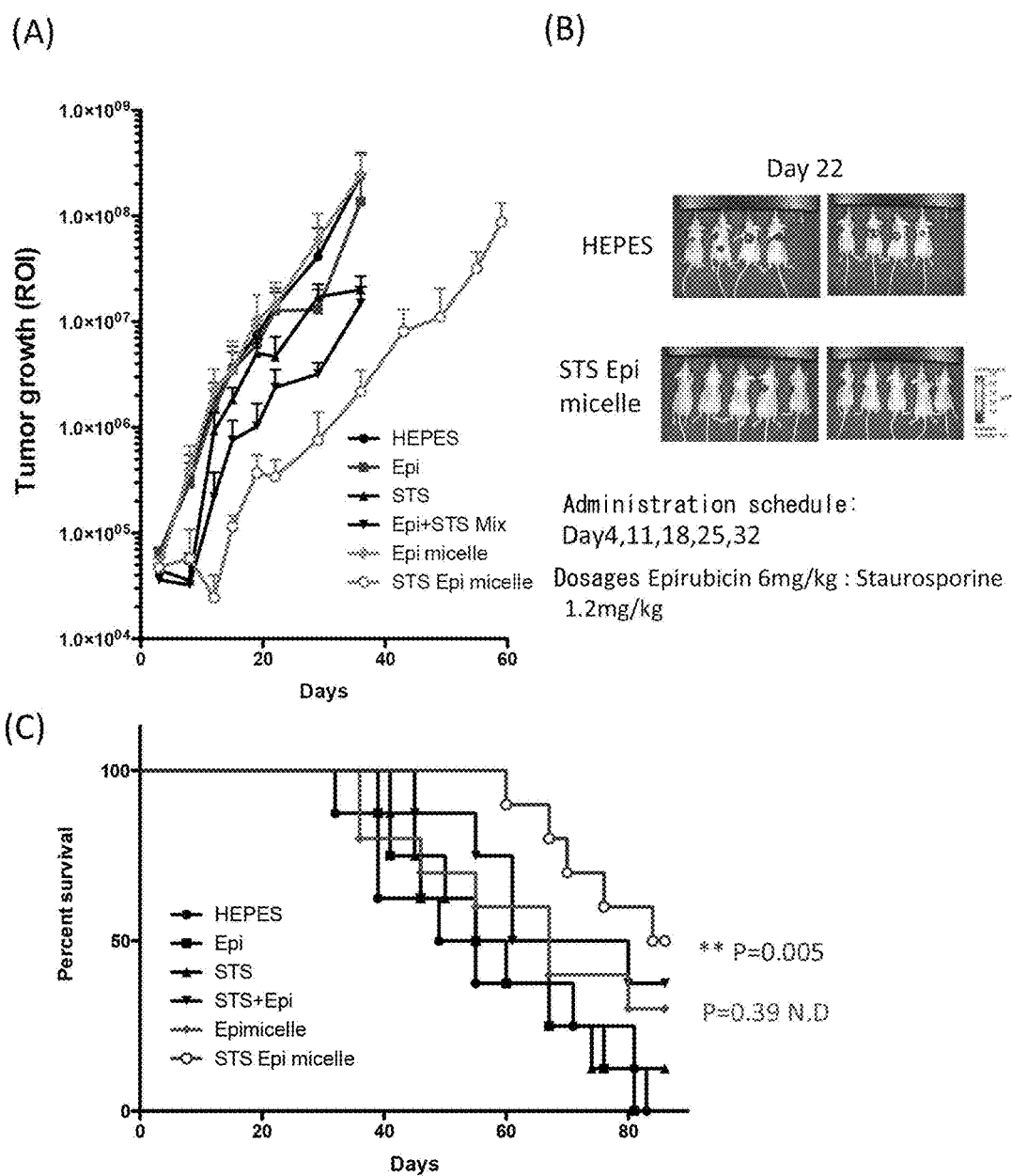
FIG. 8 indicates changes in the fluorescence intensity of luciferase in the case of having intravenously administered epirubicin (Epi), staurosporine (STS), mixture of staurosporine and epirubicin (STS+Epi Mix), epirubicin micelle (Epi micelle) and staurosporine-incorporating epirubicin micelle (STS Epi micelle) in an orthotopic model obtained by transplanting cisplatin-resistant human lung cancer strain, which is genetically modified to express luciferase, into the lungs (FIG. 8A), while FIG. 8B indicates the appearance of the luminescence of luciferase on Day 22. Moreover, FIG. 8C indicates a graph of survival rates.

HEPES solution was administered instead of a drug for use as a negative control. 200 μl of staurosporine were injected into the caudal vein after dissolving in DMSO at 5 mg/ml and diluting with physiological saline for injection (Otsuka Pharmaceutical Co., Ltd.). D-luciferin (Summit Pharmaceuticals International Corp.) was administered intraperitoneally and luminescence intensity of the luciferase was measured twice a week using an IVIS Imaging System (Summit Pharmaceuticals International Corp.) (FIG. 8A). Photographs indicating luciferase luminescence on Day 22 are shown in FIG. 8B. Survival curves were verified according to the Kaplan-Meier method using Prism software and the presence of significant differences was tested using the log-rank test.

Significant differences were not observed between the negative control and other groups such as the Epi or Epi Micelle group, and a significant difference was only observed between the negative control and STS+Epi Micelle group (P=0.005).

Example 9

Measurement of In Vivo Anti-Cancer Activity in Orthotopic Kidney Cancer Model $2 \times 10^4$ mouse kidney cancer-derived cells (Renca) (50 μl, containing 10% Matrigel) were administered into the renal capsules of Balb/c mice using the method described in Dinney, C. P., et al., Cancer Res., 1991 Jul. 15, 51(14), 3741-3747 in order to verify the effect of staurosporine micelle on kidney cancer. Four days after administering into the kidney, the drugs indicated in the following table were diluted to their prescribed dosages with physiological saline for injection (Otsuka Pharmaceutical Co., Ltd.) and administered into the caudal vein (on Days 4, 11 and 18).

TABLE 5

| Drug | Abbreviation | Staurosporine Equivalent | Epirubicin Equivalent |
| --- | --- | --- | --- |
| Epirubicin | Epi | — | 6 mg/kg |
| Staurosporine | STS | 1.2 mg/kg | — |
| Staurosporine and epirubicin mixture | STS Epi Mix | 1.2 mg/kg | 6 mg/kg |
| Epirubicin micelle | EPI Micelle | — | 6 mg/kg |
| Staurosporine-incorporating epirubicin micelle prepared in Example 1 | STS + Epi Micelle | 1.2 mg/kg | 6 mg/kg |

HEPES solution was administered instead of a drug for use as a negative control. 200 μl of staurosporine were injected into the caudal vein after dissolving in DMSO at 5 mg/ml and diluting with physiological saline for injection (Otsuka Pharmaceutical Co., Ltd.). The days in which the animals died were recorded, and survival curves were verified according to the Kaplan-Meier method using Prism software and the presence of significant differences was tested using the log-rank test.

Significant differences were observed between the negative control and Epi (P=0.0001), between Epi and Epi Micelle (P<0.0001), and between Epi Micelle and STS+Epi Micelle (P=0.0073). Sixty days later, the diameters of tumors that had metastasized to the lung were measured by 3DμCT (R-mCT2m, Rigaku Corp., Japan) for the experimental animals, or in the case an animal had died, the radius was measured directly following autopsy followed by determination of tumor volume (using the equation $4/3 \times \pi \times r^3$). A significant difference (P=0.046) was observed for lung metastatic tumor volume between Epi micelle and STS+Epi micelle (FIGS. 9A to 9D). Moreover, the number of cells expressing the stem cell marker, CD105, was measured by flow cytometry. The number of cells expressing CD105 was shown to be reduced by the staurosporine-incorporating epirubicin micelle (FIG. 9E).

Example 10

Measurement of In Vitro Anti-Cancer Activity

Figure 10:
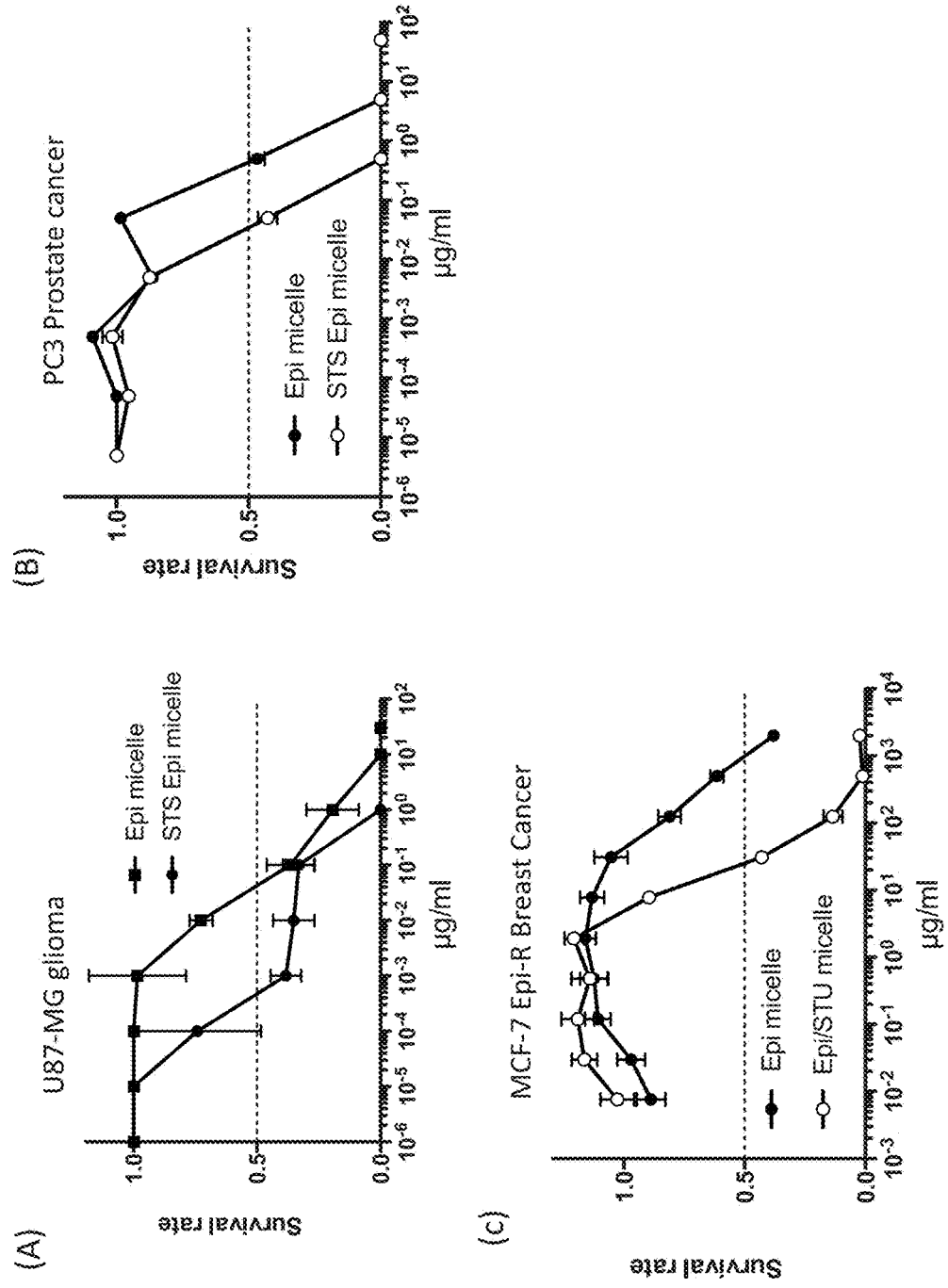
FIG. 10 indicates the efficacy of an epirubicin micelle and staurosporine-incorporating epirubicin micelle in vitro against glioma (FIG. 10A), prostate cancer (FIG. 10B) cells and epirubicin-resistant breast cancer cell (FIG. 10C). In the case of either cancer, the staurosporine-incorporating epirubicin micelle was shown to demonstrate higher efficacy.

Anti-cancer activity was measured according to the method indicated below using the Cell Counting Kit-8 (Dojindo, Japan). Glioma cell line (U87-MG) cells, prostate cancer cell line (PC3) cells and epirubicin-resistant breast cancer cell line (U87-MG) cells were respectively disseminated at $1 \times 10^3$ cells/well to $3 \times 10^3$ cells/well. The medium was replaced on the following day followed by the addition of 50 μl of medium. Moreover, dilution series of epirubicin micelle or the staurosporine-incorporating epirubicin micelle prepared in Example 1 were prepared and 50 μl of solution were added to wells containing the cells followed by stirring. 72 hours later, 10 μl of Cell Counting Kit-8 were added followed by measuring optical absorbance at 450 nm 1 hour later with a microplate reader (Model 680, BioRad, Hercules, Calif.). Cell survival rates (%) were calculated by applying the measured optical absorbance to the equation shown below (FIGS. 10A to 10C). These were plotted on the graph for each drug and the value corresponding to a survival rate of 50% was taken to be the $IC_{50}$ value.

$$\text{Cell survival rate } (\%) = [(As-Ab)/(Ac-Ab)] \times 100 \quad \text{[Equation 3]}$$

In the equation, As indicates the optical absorbance of the specimen (wells containing cells, test substance and Cell Counting Kit solution), Ac indicates the optical absorbance of a negative control (wells containing only cells and Cell Counting Kit solution), and Ab indicates the optical absorbance of a blank (wells containing only medium and Cell Counting Kit solution without containing cells).

The $IC_{50}$ values of each of the drugs tested were significantly lower than the staurosporine-incorporating epirubicin micelle for the three cancer cell lines.

Example 11

Figure 11:
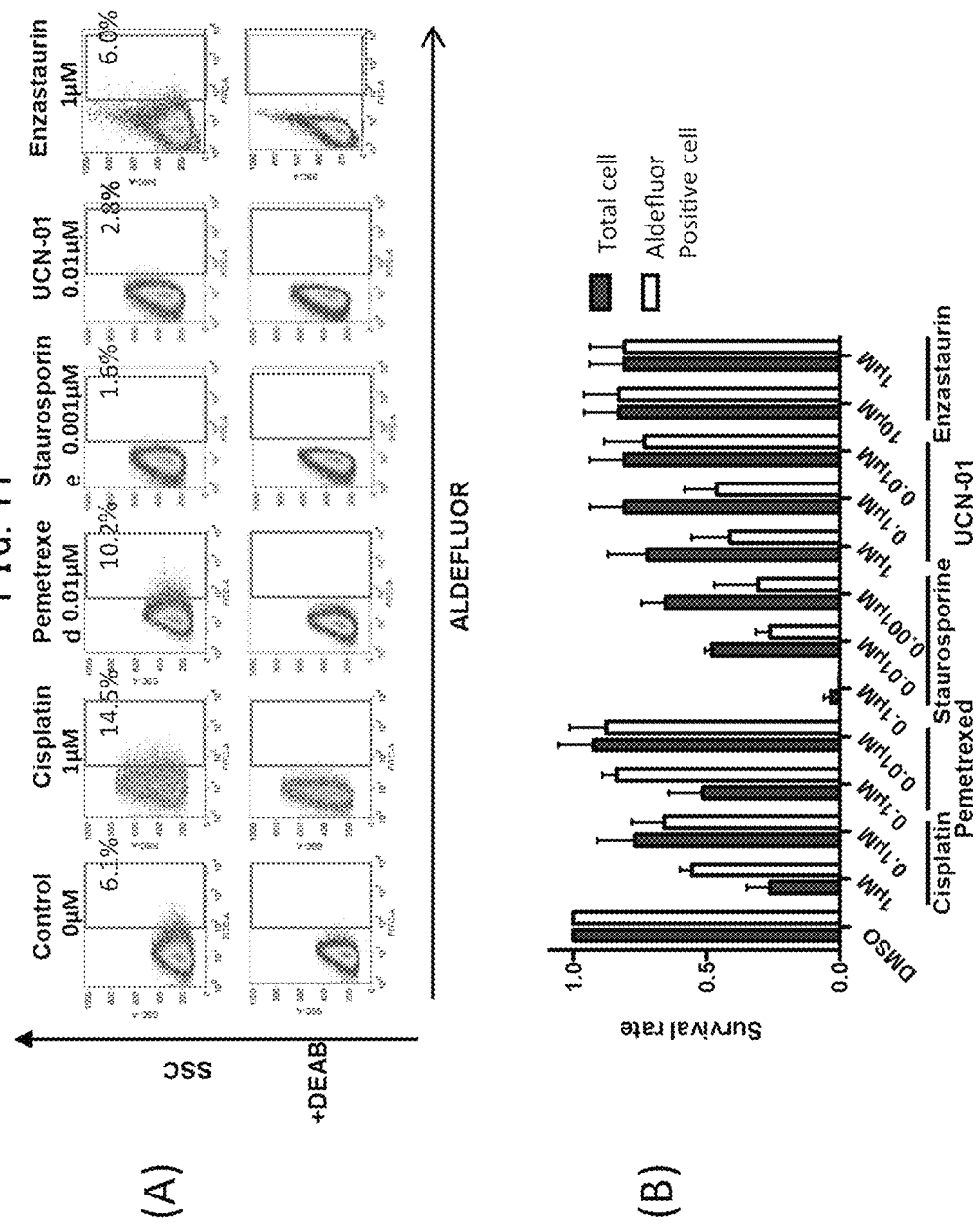
FIG. 11 depicts graphs indicating the effects of various drugs (cisplatin, pemetrexed, staurosporine, UCN-01 and enzastaurin) against cancer stem cells contained in MSTO-211H mesothelioma cells, which is resulted from FACS (FIG. 11A). The vertical axis of FIG. 11A indicates side-scattered light (SSC), the horizontal axis indicates Aldefluor-positive cells, the upper row indicates the distributions of cell populations following the addition of each drug, while the lower row indicates the distributions of cell populations following addition of an ALDH inhibitor in the form of DEAB.

Efficacy of Indolocarbazole Compounds on Cancer Stem Cells in Mesothelioma $2 \times 10^5$ mesothelioma (MST0211) cells were disseminated followed by not adding drug (control) or adding 1 μM cisplatin (Yakult Honsha Co., Ltd., Japan), 0.01 µM pemetrexed, 0.001 µM staurosporine, 0.01 µM UCN-1 or 1 µM enzastaurin and incubating for 72 hours or 24 hours. The incubated cells were then analyzed by FACS (BD LSR II, Becton Dickinson) using an Aldefluor Assay (StemCell Technologies, Durham, N.C., USA) and adding 15 µM diethylaminobenzaldehyde (DEAB) as a negative control followed by graphically representing the results by plotting side-scattered light (SSC) on the vertical axis and plotting Aldefluor-positive cells on the horizontal axis (FIG. 11A). The lower row indicates the results of FACS when having added an ALDH inhibitor in the form of DEAB. In the case of cisplatin and pemetrexed, which are indicated for mesothelioma, the proportion of Aldefluor-positive cells increased, and although cancer cells were decreased by these drugs, cancer stem cells were shown to end up remaining. On the other hand, in the case of staurosporine and UCN-01, the number of Aldefluor-positive cells decreased, thereby indicating that these drugs are also effective against cancer stem cells.

Example 12

Expression of ABC Transporter in Resistant Strains and Inhibition of ABC Transporter by Staurosporine Expression of ABC Transporter (MDR-1) by Resistant Strains Cell populations expressing MDR-1 were measured with a flow cytometer (BD LSR II, BD Biosciences) using anti-MDR-1-PE (Biolegend) for cultured epirubicin-resistant breast cancer cells (MCF-7) and cisplatin-resistant lung cancer cells (H460) before and after acquiring resistance (FIGS. 13A and 14A). Cells expressing MDR-1 were shown to increase as a result of acquiring resistance.

Elimination of Epirubicin by Resistant Strains and Suppression of Elimination of Epirubicin by Staurosporine Epirubicin-resistant breast cancer cells (MCF-7) and cisplatin-resistant lung cancer cells (H460) were respectively disseminated in each of the wells of an 8-well Tek chambered cover glass (Thermo Fisher Scientific K.K.) at 1×10$^4$ cells/well followed by culturing overnight. The medium was then replaced with 200 µl of RPMI1640 (phenol red-free) containing 0.1 µg/ml of Hoechst 33342 and 10% FBS. Next, the drugs indicated below were added to the final concentrations indicated in the table.

TABLE 6

| Drug | Abbreviation | Staurosporine Equivalent | Epirubicin Equivalent |
| --- | --- | --- | --- |
| Epirubicin | Epi | — | 3 µg/ml |
| Staurosporine and epirubicin mixture | STS Epi Mix | 3 µg/ml | 0.6 µg/ml |
| Epirubicin micelle | EPI Micelle | — | 0.6 µg/ml |
| Staurosporine-incorporating epirubicin micelle prepared in Example 1 | STS + Epi micelle | 3 µg/ml | 0.6 µg/ml |
| 1 µg/ml verapamil | Verapamil | — | — |

200 µl of eFluxx-ID-GFP solution were added 1 hour after addition of drug. The medium was replaced with RPMI1640 medium containing 10% FBS 30 minutes after addition followed by observation with an LSM780 confocal microscope and taking photographs thereof (FIGS. 12B and 13B). Cells subjected to the procedure prior to acquiring resistance were used as a control and epirubicin was added for the drug. In this experiment, fluorescence-labeled epirubicin (manufacturer) was used for the epirubicin. Although epirubicin and eFluxx-ID-GFP were localized within cells prior to acquiring resistance, the epirubicin and epirubicin micelle were eliminated from the cells in the resistant strains. In the case of using a mixture of epirubicin and staurosporine or staurosporine-incorporating epirubicin micelle for the drug, both epirubicin and eFluxx-ID-GFP were shown to be present within the cells, while ABC transporter was shown to be inhibited by staurosporine. Furthermore, verapamil is a type of ABC transporter inhibitor, and eFluxx-ID-GFP was shown to be localized within the cells in the case of having added verapamil.

Suppression of Drug Elimination Activity of Drug-Resistant Tumor Cell Lines

Drug elimination activity was investigated with the eFluxx-ID Green Multidrug Resistance Assay Kit (Enzo Life Science) using tumor cells lines consisting of (A) epirubicin-resistant mesothelioma (MSTO-211) cells, (B) epirubicin-resistant breast cancer (MCF-7) cells, (C) cisplatin-resistant lung cancer (H460) cells, (D) cancer cells highly expressing BCRP (Hela cells), and (E) cells highly expressing MRP (A549) (FIGS. 14A to 14E). More specifically, after detaching each of the cultured cells by incubating in trypsin-EDTA solution, the cells were washed with medium to obtain cell suspensions having a concentration of 1×10$^4$ cells/ml. The cell suspensions were pre-warmed at 37° C. for 10 minutes or longer followed by adding the following drugs to the final concentrations indicated to 250 µl of the cell suspensions (2.5×10$^5$ cells): MDR-1 inhibitor in the form of verapamil (30 µm), 30 µM staurosporine (STS), 30 µM epirubicin micelle (Epi Micelle) and 30 µM staurosporine-incorporating epirubicin micelle (STS-Epi micelle) were added to cell lines (A) to (C), BCRP inhibitor in the form of novobiocin (400 µM), 30 µM staurosporine (STS) and 30 µM staurosporine-incorporating epirubicin micelle (STS-Epi micelle) were added to cells (D), and MRP inhibitor in the form of MK-571 (200 µM), 30 µM staurosporine (STS) and 30 µM staurosporine-incorporating epirubicin micelle (STS-Epi micelle) were added to cells (E). 125 µl of eFluxx-ID-GFP solution were added 1 hour after addition of drug at the concentration directed in the kit. Following addition, the cell suspensions were incubated for 30 minutes at 37° C. followed by the addition of DAPI at a final concentration of 0.5 µg/ml and analyzing with a flow cytometer (BD LSR II, BD Biosciences). MAF values shown in the figures refer to the multidrug resistance activity factor (MAF) calculated from the mean fluorescence intensity of flow cytometry, and a high value for MAF indicates a greater inhibitory effect on ABC transporters. The calculation formulas were as indicated below:

$$MAF_{MDR-1} = 100 \times (F_{MDR-1} - F0)/F_{MDR-1}$$

$$MAF_{MRP} = 100 \times (F_{MRP} - F0)/F_{MRP}$$

$$NAF_{BCRP} = 100 \times (F_{BCRP} - F0)/F_{BCRP} \qquad \text{[Equation 4]}$$

(wherein, F represents the mean flow cytometry value during addition of inhibitor, and F0 represents the mean flow cytometry value when inhibitor is not added).

The invention claimed is:
1. A pH-sensitive micelle comprising a compound which is an anti-cancer agent, and an epirubicin-conjugated copolymer, in which epirubicin or a salt thereof is bound to a block copolymer represented by the following Chemical Formula (I) or Chemical Formula (II) via hydrazide groups of the block copolymer, and wherein as a result of binding epirubicin or salt thereof, units having a hydrazide group in a side chain account for more than 0% to no more than 35% of the total number of polyamino acid units in the block copolymer:

[Chemical Formula 1]

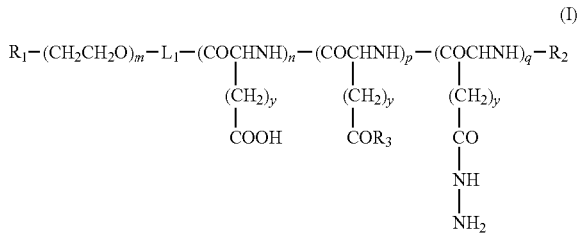

or

[Chemical Formula 2]

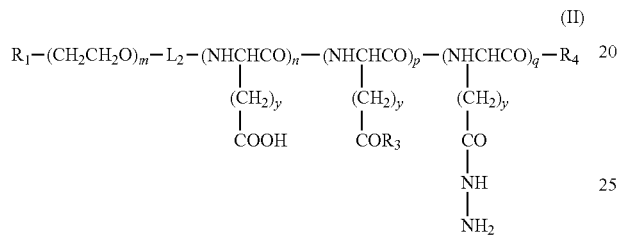

wherein,
each $R_1$ independently represents a hydrogen atom, methoxy group, methyl group, substituted linear, branched or cyclic $C_1$-$C_{12}$ alkyl group, in which the substituent is a functional group selected from the group consisting of a maleimido group, amino group, carboxyl group, thiol group, hydroxyl group and ester, wherein the substituent is unprotected or protected,
$R_2$ represents a hydrogen atom, saturated or unsaturated $C_1$-$C_{30}$ aliphatic carbonyl group or arylcarbonyl group,
$R_3$ represents —O—$R_5$ or —NH—$R_5$ in which $R_5$, which may be the same or different, represents a hydrophobic group,
$R_4$ represents a hydroxyl group, saturated or unsaturated $C_1$-$C_{30}$ aliphatic oxy group or aryl-lower alkyloxy group,
$L_1$ and $L_2$ independently from each other represents a linker,
m represents an integer of 5 to 1000,
n represents an integer of 0 to 1000,
p represents an integer of 1 to 1000,
q represents an integer of 1 to 1000,
provided that in the case units having a hydrophobic group in a side chain thereof account for 25% to 75% of the total number of polyamino acid units in the block copolymer and units having a carboxylic acid group are present in a side chain thereof, units having a carboxylic acid group in a side chain thereof, units having a hydrophobic group in a side chain thereof and units having a hydrazide group in a side chain thereof are randomly distributed throughout the entire polyamino acid region, while in the case units having a carboxylic acid group in a side chain thereof are not present, units having a hydrophobic group in a side chain thereof and units having a hydrazide group in a side chain thereof are randomly distributed throughout the entire polyamino acid region, and
y represents an integer of 1 or 2, and
wherein said anti-cancer agent is a compound having an indolocarbazole backbone.

2. The micelle according to claim 1, wherein $R_5$ is a hydrophobic group selected from the group consisting of a benzyl group, phenyl group, $C_4$-phenyl group and $C_8$-$C_{16}$ alkyl group.

3. The micelle according to claim 1, wherein epirubicin is bound to hydrazide groups at a number equal to 10% to 50% of the total number of polyamino acid units.

4. The micelle according to claim 3, wherein epirubicin is bound to hydrazide groups at a number equal to 10% to 40% of the total number of polyamino acid units.

5. The micelle according to claim 1, wherein the compound which is an anti-cancer agent is an anti-cancer stem cell agent.

6. The micelle according to claim 1, wherein the compound having an indolocarbazole backbone is a compound represented by the following formula:

[Chemical Formula 3]

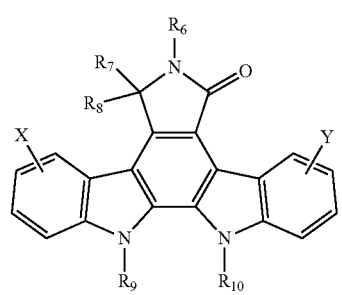

wherein,
X and Y independently represent H, OH, Cl, a propoxy group or ethylthiomethyl group,
$R_6$ represents H, a $C_{1-3}$ alkyl group, —$NH_2$, benzyl group,

[Chemical Formula 4]

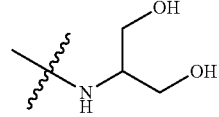 [SMILES: *NC(CO)CO]

Or

[Chemical Formula 5]

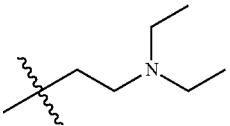

$R_7$ and $R_8$ independently from each other represent H, —OH or a methoxy group, or together with each other form O=,
$R_9$ and $R_{10}$ respectively represent a hydrogen atom, methyl group, β-D-glucopyranosyl group, 4-O-methyl-β-D-glucopyranosyl group, cyanoethyl group, or

[Chemical Formula 6]

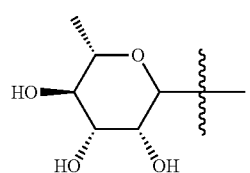

or together with each other form

[Chemical Formula 7]

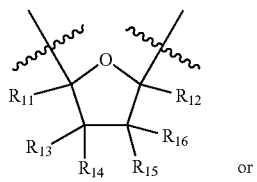 or

[Chemical Formula 8]

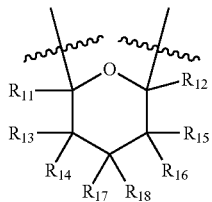

wherein $R_{11}$ represents a methyl group, $R_{12}$ represents H, $R_{13}$ and $R_{14}$ independently from each other represent H, a methoxy group, —OH, a hydroxymethyl group, methylcarboxylate group, methylamino group, methylaminomethyl group, propylaminomethyl group, dimethylaminomethyl group or

[Chemical Formula 9]

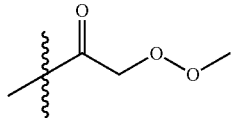

$R_{15}$ and $R_{16}$ independently from each other represent H, OH or

[Chemical Formula 10]

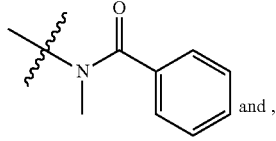 and, $R_{17}$ and $R_{18}$ represent H, OH, methylamino groups, dimethylamino groups, oxime groups, or

[Chemical Formula 11]

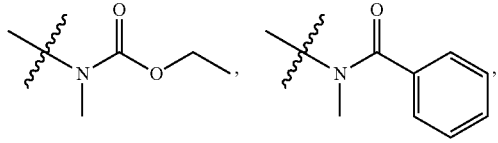

-continued

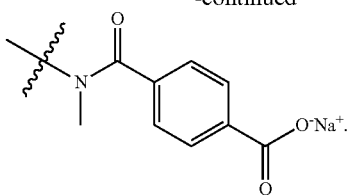

7. The micelle according to claim 1, wherein the compound having an indolocarbazole backbone is at least one compound selected from the group consisting of staurosporine, 7-hydroxystaurosporine, KT5926 (CAS:126643-38-7), staurosporine aglycone, SF2370 (K252a, CAS: 99533-80-9), KT5823 (CAS:126643-37-6), 4'-N-benzoylstaurosporine, PKC412 (CAS:120685-11-2), Go6976 (CAS:136194-77-9), N,N-dimethylstaurosporine, N-ethoxycarbonyl-7-oxostaurosporine, KT-6124 (CAS: 118777-50-7), CGP42700 (CAS:121578-39-0), 4'-demethylamino-4',5'-dihydroxystaurosporine, 7-oxostaurosporine, CEP751 (CAS:156177-59-2), NA0346 (CAS:120925-61-3), NA0359 (CAS:134931-91-2), 3'-demethoxy-3'-hydroxystaurosporine, KT 6006 (a 3,9-bis-hydroxy derivative of K252a), 7-O-methyl-UCN 01

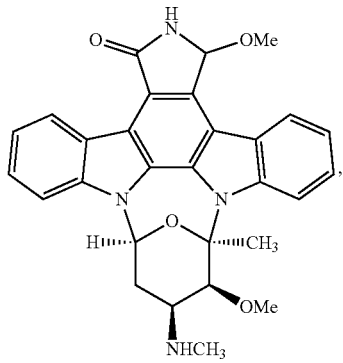

TAN 999 (CAS:126221-75-8), NA 0345 (CAS:120925-60-2), NA 0344 (CAS:120925-59-9),

CGP 44171A

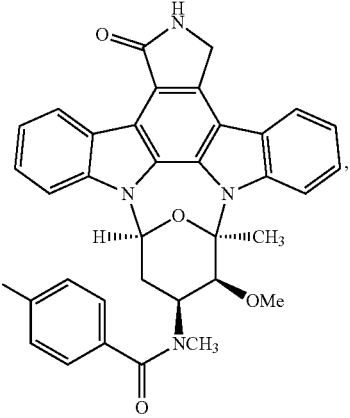

-continued

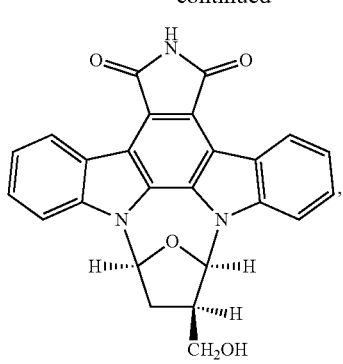

SCH 47112

N,N-dimethylstaurosporine, TAN 1030A (CAS:126221-76-9), lestaurtinib, 4'-demethylamino-4'-hydroxystaurosporine, AFN941 (CAS:220038-19-7), edotecarin, becatecarin, and salts thereof.

8. The micelle according to claim 7, wherein the compound having an indolocarbazole backbone is at least one compound selected from the group consisting of staurosporine, 7-hydroxystaurosporine, PKC412 (CAS:120685-11-2) and lestaurtinib.

9. The micelle according to claim 1, wherein the weight ratio of the epirubicin-conjugated copolymer and the anticancer agent is 5:2 to 10:1.

10. A pharmaceutical composition for treating cancer or a tumor, comprising the micelle according to claim 1.

11. The pharmaceutical composition according to claim 10, wherein the cancer or tumor is selected from the group consisting of neuroblastoma, liver cancer, malignant melanoma, uterine cancer, bladder cancer, bile duct cancer, esophageal cancer, osteosarcoma, testicular tumor, thyroid cancer, acute myelogenous leukemia, brain tumor, prostate cancer, pancreatic cancer, head and neck squamous cell carcinoma, mesothelioma, lung cancer, colon cancer, kidney cancer, ovarian cancer and breast cancer.

12. The composition according to claim 10, which is effective against cancer or tumors containing cancer stem cells.

13. The composition according to claim 12, wherein the cancer or tumor containing cancer stem cells is at least one cancer selected from the group consisting of acute myelogenous leukemia, brain tumor, prostate cancer, pancreatic cancer, head and neck squamous cell carcinoma, mesothelioma, lung cancer, colon cancer, kidney cancer, ovarian cancer and breast cancer.

14. The micelle according to claim 1, wherein the compound having indolocarbazole backbone is staurosporine.

15. A method for treating a subject suffering from cancer or a tumor, comprising administering a therapeutically effective amount of the micelle according to claim 1 to the subject.

16. The method according to claim 15, wherein the cancer or tumor is selected from the group consisting of neuroblastoma, liver cancer, malignant melanoma, uterine cancer, bladder cancer, bile duct cancer, esophageal cancer, osteosarcoma, testicular tumor, thyroid cancer, acute myelogenous leukemia, brain tumor, prostate cancer, pancreatic cancer, head and neck squamous cell carcinoma, mesothelioma, lung cancer, colon cancer, kidney cancer, ovarian cancer and breast cancer.

17. The method according to claim 15, which is effective against cancer or tumors containing cancer stem cells.

18. The method according to claim 15, wherein the cancer or tumor containing cancer stem cells is at least one cancer selected from the group consisting of acute myelogenous leukemia, brain tumor, prostate cancer, pancreatic cancer, head and neck squamous cell carcinoma, mesothelioma, lung cancer, colon cancer, kidney cancer, ovarian cancer and breast cancer.

* * * * *